US008263350B2

(12) United States Patent
Koide et al.

(10) Patent No.: US 8,263,350 B2
(45) Date of Patent: Sep. 11, 2012

(54) MOLECULAR AFFINITY CLAMP TECHNOLOGY AND USES THEREOF

(75) Inventors: Shohei Koide, Chicago, IL (US); Jin Huang, Beijing (CN); Akiko Koide, Chicago, IL (US)

(73) Assignee: The University of Chicago, Chicago, IL (US)

( * ) Notice: Subject to any disclaimer, the term of this patent is extended or adjusted under 35 U.S.C. 154(b) by 136 days.

(21) Appl. No.: 12/826,322

(22) Filed: Jun. 29, 2010

(65) Prior Publication Data
US 2011/0045604 A1 Feb. 24, 2011

Related U.S. Application Data

(60) Provisional application No. 61/221,358, filed on Jun. 29, 2009.

(51) Int. Cl.
*G01N 33/53* (2006.01)
(52) U.S. Cl. .......................................... 435/7.1; 435/518
(58) Field of Classification Search .................. None
See application file for complete search history.

(56) References Cited

U.S. PATENT DOCUMENTS
2003/0170615 A1    9/2003   Ustav et al. ........................ 435/5

FOREIGN PATENT DOCUMENTS
WO    WO 2009/062170    5/2009

OTHER PUBLICATIONS

Starkenburg et al. (Applied Environmental Microbiology 2006 vol. 72, p. 2050-2063).*
Huang et al., "A peptide tag system for facile purification and single-molecule immobilization," *Biochemistry*, 48:11834-11836, 2009.
Huang et al., "Design of protein function leaps by directed domain interface evolution," *Proc. Natl. Acad. Sci. USA*, 105:6578-83, 2008.
Koide and Koide, "Monobodies: antibody mimics based on the scaffold of the fibronectin type III domain," *Methods Mol. Biol.*, 352:95-109, 2007.
Koide et al., "The fibronectin type III domain as a scaffold for novel binding proteins," *J. Mol. Biol.*, 284:1141-1151, 1998.
Laura et al., "The Erbin PDZ domain binds with high affinity and specificity to the carboxyl termini of delta-catenin and ARVCF," *J. Biol. Chem.*, 277:12906-14, 2002.
Sidhu and Koide, "Phage display for engineering and analyzing protein interaction interfaces," *Curr. Opin. Struct. Biol.*, 17:481-7, 2007.
Skelton et al., "Origins of PDZ domain ligand specificity. Structure determination and mutagenesis of the Erbin PDZ domain," *J. Biol. Chem.*, 278:7645-54, 2003.
Zhang et al., "Convergent and divergent ligand specificity among PDZ domains of the LAP and zonula occludens (ZO) families," *J. Biol. Chem.*, 281:22299-311, 2006.

* cited by examiner

*Primary Examiner* — Jacob Cheu
(74) *Attorney, Agent, or Firm* — Fulbright & Jaworski L.L.P.

(57) ABSTRACT

The invention provides a molecular affinity clamp. The architecture of the affinity clamp is modular with two biorecognition modules, each capable of binding a target motif. The first biorecognition module has a recognition domain that possesses inherent or natural specificity for the target motif. The second biorecognition module also has a recognition domain that binds the motif. The two biorecognition modules are tethered together either directly, e.g., via a peptide bond between the two modules, or indirectly, e.g., via a linker moiety or linker. The invention further provides a novel affinity ligand which is specifically bound by the molecular affinity clamps of the invention.

20 Claims, 8 Drawing Sheets

Figure 1:
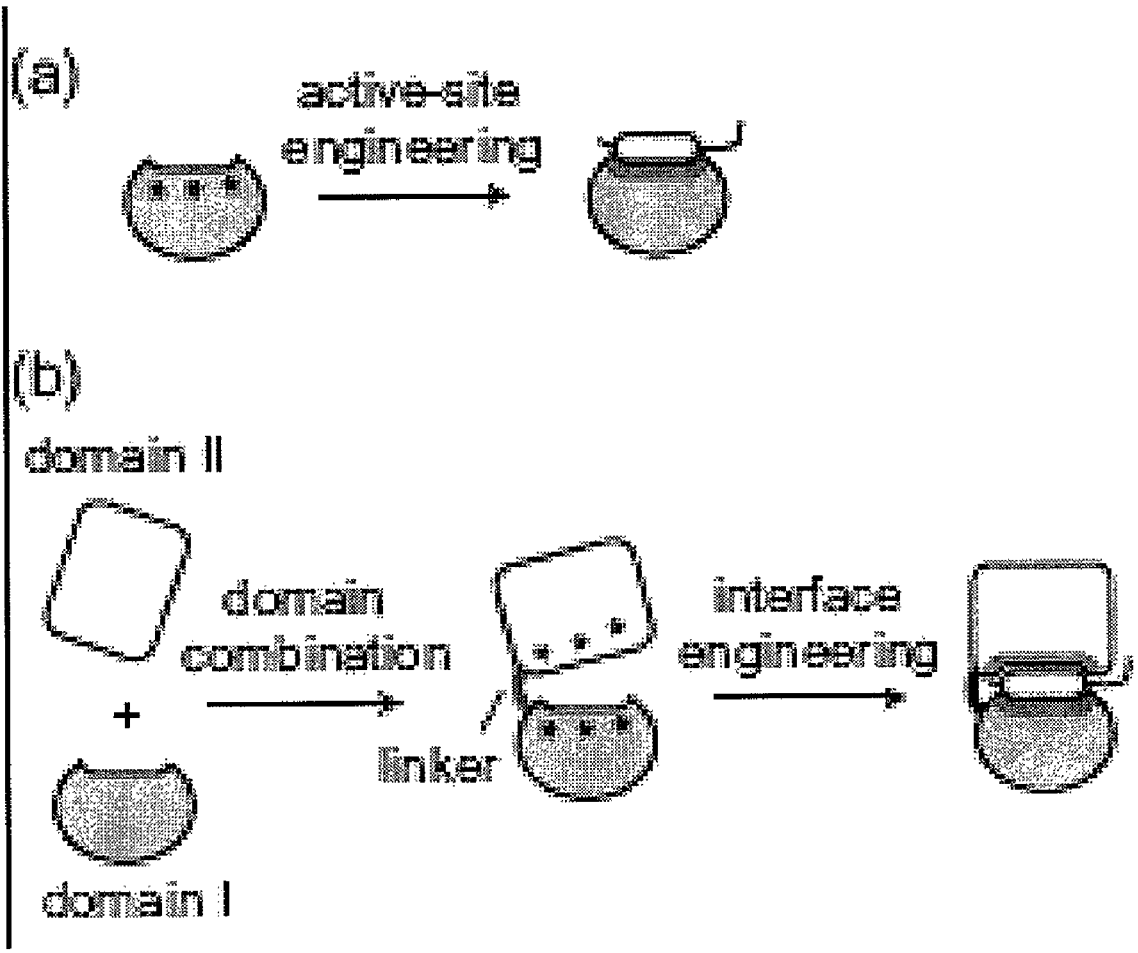

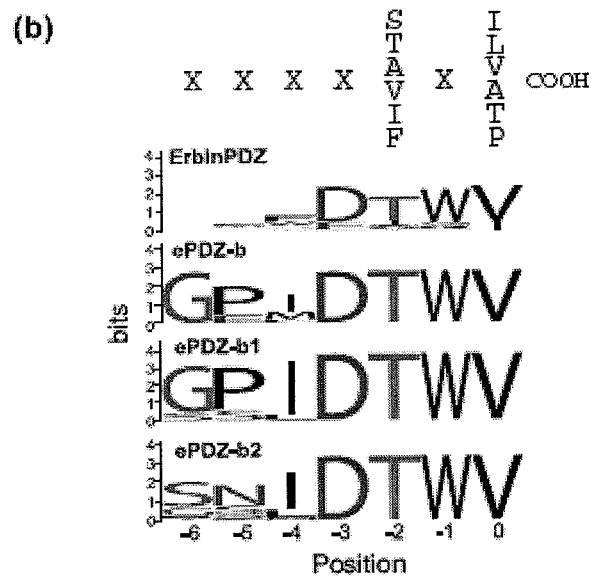
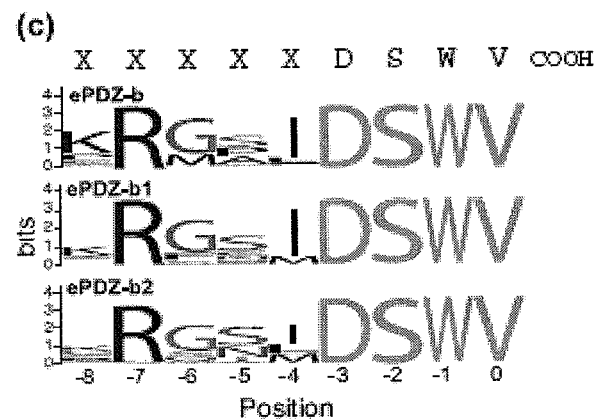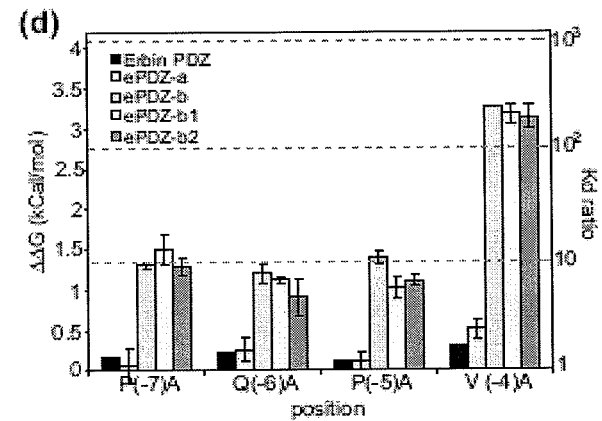
FIG. 2

(a) Library 1  XXXX(STAVIF)X(ILVATP)

| ePDZ-b | | ePDZ-b1 | | ePDZ-b2 | |
|---|---|---|---|---|---|
| GEIDTWV | 2 | SPIDTWV | 3 | SNIDTWV | 6 |
| GPMDTWV | 3 | GPIDTWV | 11 | SQIDTWV | 2 |
| GPLDTWV | 1 | GSIDTWV | 4 | SNLDTWV | 3 |
| GPIDTWV | 3 | GPLDTWV | 2 | RNIDTWV | 1 |
| | | | | GSIDTWV | 3 |
| | | | | TSIDTWV | 1 |
| | | | | GPMDTWV | 1 |

(b) Library 2  XXXXXDSWV

| ePDZ-b | | ePDZ-b1 | | ePDZ-b2 | |
|---|---|---|---|---|---|
| KRGSIDSWV | 4 | NRGRMDSWV | 1 | QRGNIDSWV | 1 |
| ERGAIDSWV | 1 | DRGSMDSWV | 1 | TRGNIDSWV | 1 |
| ERGSIDSWV | 1 | KRGSMDSWV | 1 | RRGNIDSWV | 1 |
| PRGSIDSWV | 1 | KRGSIDSWV | 3 | QRWNIDSWV | 1 |
| KRGAIDSWV | 3 | KRSNIDSWV | 2 | KRGTIDSWV | 2 |
| KRMPIDSWV | 1 | KRFEIDSWV | 1 | RSGSIDSWV | 1 |
| KRGPIDSWV | 1 | KRFNIDSWV | 1 | ERSSIDSWV | 1 |
| PRMPIDSWV | 1 | ERFSIDSWV | 1 | ERQSIDSWV | 1 |
| DRMPFDSWV | 1 | KRGQIDSWV | 1 | KRSNMDSWV | 1 |
| KRMPLDSWV | 1 | FRGEIDSWV | 1 | GRGNMDSWV | 1 |
| PRGELDSWV | 1 | VRGEIDSWV | 1 | NRGQMDSWV | 1 |
| | | SRGAIDSWV | 1 | GRGSMDSWV | 1 |
| | | VRGSIDSWV | 1 | ERGSMDSWV | 1 |
| | | ARGSIDSWV | 2 | GRGSLDSWV | 2 |
| | | RRGSIDSWV | 1 | RRGSLDSWV | 1 |
| | | | | KRNSLDSWV | 1 |
| | | | | KRSSLDSWV | 1 |

FIG. 5

SEQUENCE LISTING

```
<160> NUMBER OF SEQ ID NOS: 19

<210> SEQ ID NO 1
<211> LENGTH: 8
<212> TYPE: PRT
<213> ORGANISM: Artificial Sequence
<220> FEATURE:
<223> OTHER INFORMATION: Synthetic peptide

<400> SEQUENCE: 1

Arg Gly Ser Ile Asp Thr Trp Val
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic peptide

<400> SEQUENCE: 2

His Tyr Asn Tyr His Tyr Tyr Ser
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic peptide

<400> SEQUENCE: 3

Ser Tyr Tyr Gly Val Ser
1               5

<210> SEQ ID NO 4
<211> LENGTH: 8
<212> TYPE: PRT
<213> ORGANISM: Artificial Sequence
<220> FEATURE:
```

<223> OTHER INFORMATION: Synthetic peptide

<400> SEQUENCE: 4

Pro Gln Pro Val Asp Ser Trp Val
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Glycine and/or Serine
<220> FEATURE:
<221> NAME/KEY: MISC_FEATURE
<222> LOCATION: (3)..(3)
<223> OTHER INFORMATION: Any natural occurring amino acid
<220> FEATURE:
<221> NAME/KEY: MISC_FEATURE
<222> LOCATION: (4)..(4)
<223> OTHER INFORMATION: Isoleucine, Leucine and/or Methionine

<400> SEQUENCE: 5

Arg Xaa Xaa Xaa Asp Ser Trp Val
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Glycine and/or Serine
<220> FEATURE:
<221> NAME/KEY: MISC_FEATURE
<222> LOCATION: (3)..(3)
<223> OTHER INFORMATION: Asparagine and/or Serine
<220> FEATURE:
<221> NAME/KEY: MISC_FEATURE
<222> LOCATION: (4)..(4)
<223> OTHER INFORMATION: Isoleucine, Leucine and/or Methionine

<400> SEQUENCE: 6

Arg Xaa Xaa Xaa Asp Ser Trp Val
1               5

<210> SEQ ID NO 7
<211> LENGTH: 4
<212> TYPE: PRT
<213> ORGANISM: Artificial Sequence
<220> FEATURE:
<223> OTHER INFORMATION: Synthetic peptide

<400> SEQUENCE: 7

Asp Ser Trp Val
1

<210> SEQ ID NO 8
<211> LENGTH: 7
<212> TYPE: PRT
<213> ORGANISM: Artificial Sequence
<220> FEATURE:
<223> OTHER INFORMATION: Synthetic peptide

<400> SEQUENCE: 8

```
Tyr Arg Glu Leu Pro Val Ser
1               5

<210> SEQ ID NO 9
<211> LENGTH: 4
<212> TYPE: PRT
<213> ORGANISM: Artificial Sequence
<220> FEATURE:
<223> OTHER INFORMATION: Synthetic peptide

<400> SEQUENCE: 9

Gly Ser Lys Ser
1

<210> SEQ ID NO 10
<211> LENGTH: 8
<212> TYPE: PRT
<213> ORGANISM: Artificial Sequence
<220> FEATURE:
<223> OTHER INFORMATION: Synthetic peptide

<400> SEQUENCE: 10

Pro Ala Ser Pro Asp Ser Trp Val
1               5

<210> SEQ ID NO 11
<211> LENGTH: 4
<212> TYPE: PRT
<213> ORGANISM: Artificial Sequence
<220> FEATURE:
<223> OTHER INFORMATION: Synthetic peptide

<400> SEQUENCE: 11

Asp Thr Trp Val
1

<210> SEQ ID NO 12
<211> LENGTH: 5
<212> TYPE: PRT
<213> ORGANISM: Artificial Sequence
<220> FEATURE:
<223> OTHER INFORMATION: Synthetic peptide

<400> SEQUENCE: 12

Ala Arg Val Cys Phe
1               5

<210> SEQ ID NO 13
<211> LENGTH: 4
<212> TYPE: PRT
<213> ORGANISM: Artificial Sequence
<220> FEATURE:
<223> OTHER INFORMATION: Synthetic peptide

<400> SEQUENCE: 13

Tyr Ser Ser Ser
1

<210> SEQ ID NO 14
<211> LENGTH: 10
<212> TYPE: PRT
<213> ORGANISM: Artificial Sequence
<220> FEATURE:
<223> OTHER INFORMATION: Synthetic peptide

<400> SEQUENCE: 14

Tyr Ser Asp Tyr Tyr Gly Ser His His Tyr
1               5                   10
```

-continued

```
<210> SEQ ID NO 15
<211> LENGTH: 7
<212> TYPE: PRT
<213> ORGANISM: Artificial Sequence
<220> FEATURE:
<223> OTHER INFORMATION: Synthetic peptide

<400> SEQUENCE: 15

Tyr Tyr Asp Ser His Val Ser
1               5

<210> SEQ ID NO 16
<211> LENGTH: 7
<212> TYPE: PRT
<213> ORGANISM: Artificial Sequence
<220> FEATURE:
<223> OTHER INFORMATION: Synthetic peptide

<400> SEQUENCE: 16

Phe Thr Asp Leu Pro Val Ser
1               5

<210> SEQ ID NO 17
<211> LENGTH: 5
<212> TYPE: PRT
<213> ORGANISM: Artificial Sequence
<220> FEATURE:
<223> OTHER INFORMATION: Synthetic peptide

<400> SEQUENCE: 17

Gly Gly Ser Gly Gly
1               5

<210> SEQ ID NO 18
<211> LENGTH: 4
<212> TYPE: PRT
<213> ORGANISM: Artificial Sequence
<220> FEATURE:
<223> OTHER INFORMATION: Synthetic peptide

<400> SEQUENCE: 18

Gly Gly Ser Gly
1

<210> SEQ ID NO 19
<211> LENGTH: 11
<212> TYPE: PRT
<213> ORGANISM: Artificial Sequence
<220> FEATURE:
<223> OTHER INFORMATION: Synthetic peptide

<400> SEQUENCE: 19

Gly Gly Ser Gly Gly Gly Gly Ser Gly Gly Ser
1               5                   10
```

MOLECULAR AFFINITY CLAMP TECHNOLOGY AND USES THEREOF

This application claims priority to U.S. Provisional Application No. 61/221,358 filed Jun. 29, 2009, which is incorporated herein by reference in its entirety.

This invention was made with government support under DK063090 awarded by the National Institutes of Health. The government has certain rights in the invention.

I. FIELD OF THE INVENTION

Embodiments of this invention are directed generally to biology, medicine, and protein engineering. Certain aspects of the invention are directed to affinity ligands and related reagents and methods.

II. BACKGROUND

A major bottleneck in virtually all areas of biomedical sciences and disease diagnoses is a paucity of high-quality affinity reagents. Affinity reagents are indispensable for delineating the molecular mechanisms of diseases, for detecting and characterizing cellular abnormalities, and for characterizing effects of drugs. In this post-genome era, the demand for high-quality affinity reagents is rapidly increasing across all fields of biomedical science.

Short peptide motifs are, in principle, attractive targets against which affinity reagents can be generated. Short peptides derived from a target protein or a synthetic peptide can be chemically synthesized, and the epitope or affinity ligand (the region that is recognized by an affinity reagent) can be readily deduced. Short peptide motifs (and their modification state) are not only indicators (or biomarkers) of the functional state of extremely important components of these networks, but can be used in various other assays and methodologies as affinity ligands.

Currently, antibodies are the gold standard of affinity reagents. However, making antibodies that recognize a particular short peptide motif with high affinity and specificity is difficult and time-consuming. The paucity of good antibodies to short peptides is not due to a lack of intensive effort. The difficulty arises from the fundamental thermodynamics of the binding of a short flexible peptide motif in which a small number of antibody-motif contacts must compensate for a large loss of conformational entropy. This is, perhaps, not so surprising because antibodies have not evolved specifically to bind short peptide motifs.

Antibodies have additional serious limitations. Monoclonal antibody production is low throughput and expensive and polyclonal antibodies have a fundamental problem in production scalability and archiving. Although many monoclonal antibodies to whole protein antigens exist, very few are available for defined short peptide motifs.

As to polyclonal antibodies, which are widely used, the upfront costs and efforts to generate such antibodies are low. Polyclonal antibodies do not, however, meet the criteria for high-performance affinity reagents. A polyclonal antibody is impossible to reproduce with the identical properties once the stock is depleted, making it unfeasible to establish a robust standard assay that can be broadly distributed. Further, the inherently heterogeneous nature of a polyclonal antibody makes it impossible to define precisely its properties such as motif specificity and affinity. Polyclonal antibodies also cannot be easily reformatted for different applications.

In the last decade, nucleic acid-based affinity reagents have been developed (Rimmele, 2003; Yan et al., 2005). However, they share the same difficulty as antibodies in generating high-affinity binders to short peptide motifs. To date, no nucleic acid aptamers have been generated that have low nM Kd to a short peptide motif derived from a natural protein.

Each of the current approaches for designing affinity reagents has numerous disadvantages and fails to generate high-performance affinity reagents to small peptide motifs that are critically important. There remains a need for additional affinity reagents.

SUMMARY OF THE INVENTION

The inventors have developed a new platform technology for affinity reagents. The affinity reagents embodying the principles of the invention possess affinity and specificity for short peptide target motifs of interest. These affinity reagents are termed "modular molecular affinity clamps" or "affinity clamps" because they have a clamp-like or clamshell architecture and are composed of two discrete modules or domains. One module or domain is a "specificity" domain (or "shell") engineered from a natural binding domain, e.g., protein-interaction domain, which possesses inherent class specificity. The other domain is an "enhancer" domain which is an engineered single-domain antibody mimic. The domains or modules are connected to each other through a linker. The linker can be a polypeptide linker. The linker couples the domains directly or indirectly. The domains or modules each bind the same target peptide motif. The specificity of the "specificity shell" can be enhanced by >2,000 fold and the affinity can be increased >2,000 fold. As used herein, the term "affinity" refers to the equilibrium constant for the reversible binding of two agents and is expressed as Kd. Affinity of a binding protein to a ligand can be, for example, from about 100 nanomolar (nM) to about 0.1 nM, from about 100 nM to about 1 picomolar (pM), or from about 100 nM to about 1 femtomolar (fM). As used herein, the term "avidity" refers to the resistance of a complex of two or more agents to dissociation after dilution. The term "specificity" refers to the ability of an binding agent, such as an affinity clamp, to bind preferentially to an affinity ligand versus a non-affinity ligand peptide—binding of a particular peptide is distinguishable over binding or a peptide not having a sequence of the particular peptide.

The molecular affinity clamps or affinity clamps in accordance with the invention meet a number of requirements for affinity agents, including high affinity, high specificity, high-throughput (HTP) generation, and/or scalable and economical production (See PCT application PCT/US2008/083021, which is incorporated herein by reference in its entirety). They have low nM dissociation constant(s) (Kd) for the target motifs and function well in immunochemical applications. Further, by exploiting binding-induced conformational changes, the affinity clamps can be used as label-free biosensors for diverse molecular motifs including those containing posttranslational modifications.

In other aspects, an epitope or affinity ligand can be engineered such that the affinity ligand (a short peptide sequence) is specifically recognized by a binding agent, such as an affinity clamp. These affinity ligands can be coupled to various targets. Affinity ligands coupled to targets can be used to physically manipulate or detect the target.

In certain aspects, an affinity ligand comprises or is a peptide having a carboxy terminal amino acid sequence of RGSIDTWV (SEQ ID NO:1). The affinity ligand can be encoded by a nucleic acid. The nucleic acid encoding the affinity ligand can be included in an expression cassette and/or a nucleic acid vector. The nucleic acid, expression cassette, or vector can be engineered to encode a fusion protein comprising a carboxy terminal amino acid sequence of SEQ ID NO:1. In other aspects, a host cell can comprise a nucleic acid, expression cassette, or vector of the invention. The cell can be a prokaryotic cell, e.g. a bacterial cell, or a eukaryotic cell (e.g., a mammalian or insect cell). In certain aspects the cell is a bacterial cell, e.g., an *E. coli* bacterium.

In a further aspect, a target composition can comprise a target coupled to a heterologous affinity ligand of the invention. The target can be a peptide, a polypeptide, a particle, a cell, a macromolecular complex, a small molecule, or any other moiety or entity that can be coupled to the affinity ligand of the invention. In certain aspects the affinity ligand is directly or indirectly coupled to the target. The affinity ligand can be covalently or non-covalently coupled to the target. In a particular aspect the target is a fusion protein. In yet an further aspect the affinity ligand is coupled to a label. The label can be any detectable moiety, e.g., a dye, a quencher, a reporter protein, radiolabel, or a quantum dot.

Certain embodiments are directed to fusion proteins comprising an affinity ligand, the affinity ligand having a heterologous amino acid segment comprising an amino acid sequence of RGSIDTWV (SEQ ID NO:1). In certain aspects the heterologous sequence is positioned at the carboxy terminus of the fusion protein or the carboxy terminus of the affinity ligand remains accessible or can be exposed by processing of the fusion protein. The fusion protein can further comprise a second detectable amino acid sequence, e.g., myc tag, Poly-His tag (hexa-histidine), GST tag, Flag tag, fluorescent or luminescent tag (e.g., GFP or luciferase), or any other epitope or fusion tag known to one of skill in the art. The fusion protein can further comprising a cleavage site amino terminal or carboxy terminal to the affinity ligand. The cleavage site can be a protease cleavage site, e.g., a trypsin, calpain, carboxypeptidase, chymotrypsin, V8 protease, pepsin, papain, subtilisin, thrombin, elastase, gluc-C, endo lys-C or proteinase K, caspase-1, caspase-2, caspase-3, caspase-4, caspase-5, caspase-6, caspase-7, caspase-8, MetAP-2, adenovirus protease, HIV protease site and the like.

In still further aspects the invention can be directed to an immobilization substrate comprising a binding moiety that specifically binds an affinity ligand having a carboxy terminal amino acid sequence of RGSIDTWV (SEQ ID NO:1). The binding moiety can be an antibody or an affinity clamp.

In certain aspects the invention can be directed to a detection complex comprising a target coupled to a heterologous affinity ligand having an amino acid sequence of RGSIDTWV (SEQ ID NO:1) and an agent that specifically binds the affinity ligand. The complex can further comprise at least one label. The label can be coupled to the affinity ligand, the binding agent, or both the affinity ligand and the binding agent. A label can be one or more dye, quencher, reporter protein, quantum dot or the like.

In certain aspects, the invention is directed to a method of detecting a target comprising an affinity ligand having a carboxy terminal amino acid sequence of RGSIDTWV (SEQ ID NO:1) by contacting the target with a binding agent that specifically binds the affinity ligand having a carboxy terminal amino acid sequence of RGSIDTWV (SEQ ID NO:1) and detecting the complex between the affinity ligand and the binding agent. In a further aspect, the affinity ligand is coupled to a first label and the binding agent is coupled to a second label. The first and the second label can be a donor/acceptor pair (e.g., a FRET pair). In certain aspects the binding agent is an affinity clamp that specifically binds the affinity tag having a carboxy terminal amino acid sequence of RGSIDTWV (SEQ ID NO:1).

Other aspects include methods of immobilizing a target comprising an affinity ligand having a carboxy terminal amino acid sequence of RGSIDTWV (SEQ ID NO:1) comprising contacting the target with a substrate comprising a binding agent that specifically binds the affinity ligand having a carboxy terminal amino acid sequence of RGSIDTWV (SEQ ID NO:1). The method can further comprise removing any non-specifically bound components. The method can further comprise dissociating the affinity ligand from the binding agent and/or dissociating the affinity ligand from the target.

Other aspects include methods of conjugating a first and second moiety comprising coupling to the first moiety an affinity ligand having an amino acid sequence of SEQ ID NO:1 and coupling to the second moiety an affinity ligand binding moiety that specifically binds the affinity ligand; and contacting the first and second moieties.

Other aspects include kits comprising an affinity ligand of the invention. The kits can further comprise one or more of an affinity clamp that specifically binds the affinity tag having a carboxy terminal amino acid sequence of RGSIDTWV (SEQ ID NO:1); a labeling reagent for the affinity ligand, the affinity clamp, or both the affinity ligand and the affinity clamp; and/or a label such as a dye, a quencher, a reporter protein, or a quantum dot. The affinity ligand can include a first label and an affinity ligand binding moiety comprises a second label, and the first and second label are a fluorescent resonance energy transfer (FRET) donor/acceptor pair.

In certain aspects the affinity clamp has a dissociation constant for the affinity ligand at least, at most, about, or equal to or lower than 1, 2, 3, 4, 5 µM or pM or fM.

Other embodiments of the invention are discussed throughout this application. Any embodiment discussed with respect to one aspect of the invention applies to other aspects of the invention as well and vice versa. The embodiments in the Examples section are understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or." It is also contemplated that anything listed using the term "or" may also be specifically excluded.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A and 1B is a comparison of the conventional binding-protein engineering method (FIG. 1A) and directed domain-interface evolution (FIG. 1B). (FIG. 1A) Conventional binding-protein engineering using a rigid scaffold. The interface predefined in the starting scaffold is diversified and variants with new function are selected. (FIG. 1B) Domain-interface engineering. Two domains are connected and a new recognition site is produced at the interface of the newly connected domains.

FIG. 2 illustrates specificity profiles of affinity clamps. (a) Sequences of the C-terminal peptides of ARVCF (SEQ ID NO:12) and δ-catenin. (b) and (c) Weblogo 30; 31 representations of specificity profiles for ePDZ-b family clamps. The sequence conservation at each position is represented by the overall height of the stack. The height of symbols within the stack indicates the relative frequency of each amino. The grey symbols indicate positions that were kept constant in the libraries. (b) shows the results with the hepta-peptide library and (c) with the penta-peptide library. The library design is shown above the profiles. (d) Effects of Ala substitution at the indicated positions of the ARVCF peptide as measured by SPR. The values for the free energy changes (ΔΔG) are shown on the left axis and those for the Kd ratio (Kd wt/Kd mutant) are shown on the right axis.

Figure 3:
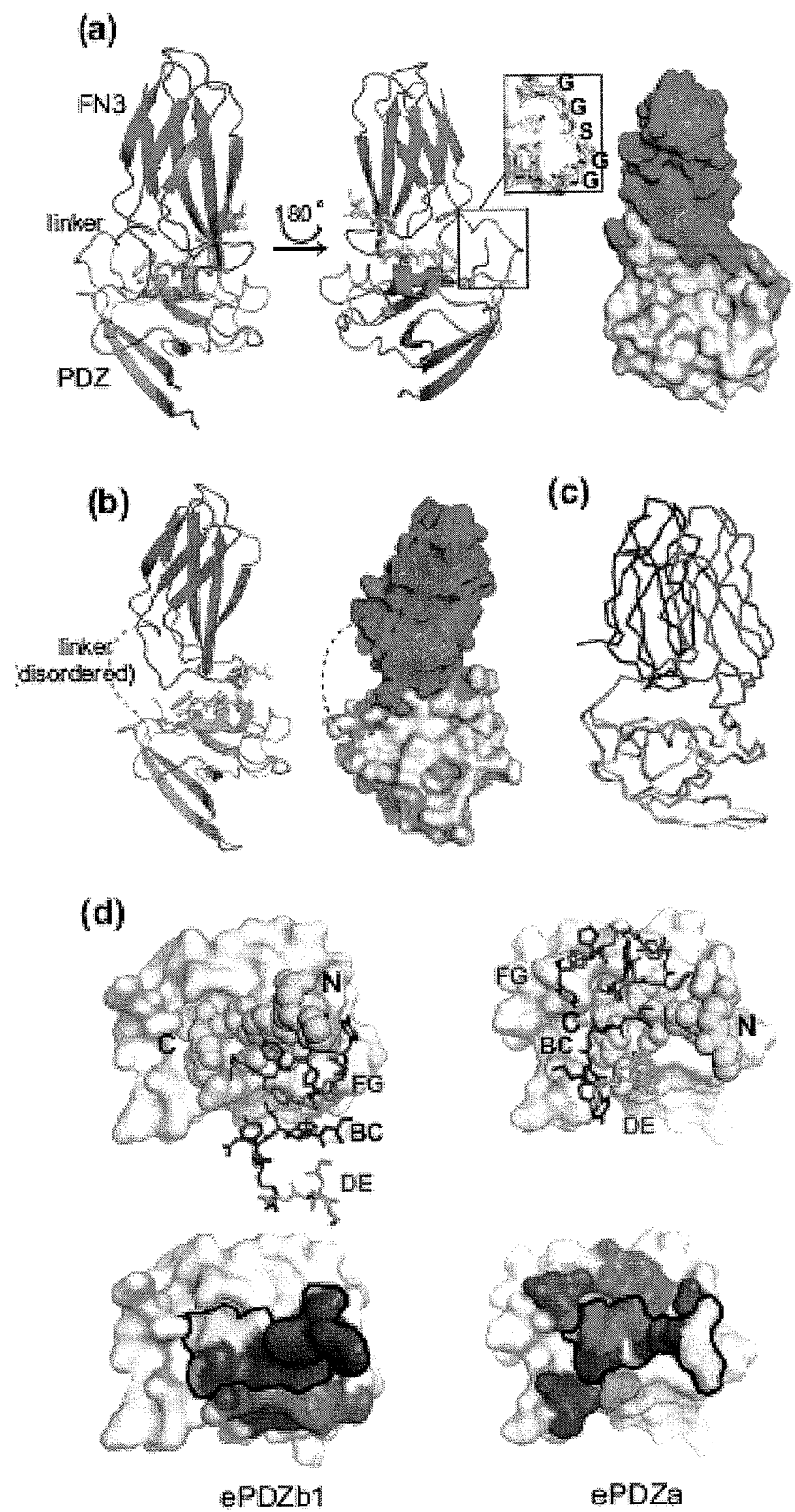

FIG. 3 illustrates X-ray crystal structures of ePDZ-b1 and ePDZ-a in complex with the ARVCF peptide. (a) and (b) Ribbon (left panel) and surface (right panel) representations of the overall structures of ePDZ-b1 (a) and ePDZ-a (b). The PDZ and FN3 portions and the peptide are shown. In ePDZ-b1, the linker of is shown. The weighted $2F_{obs}-F_{calc}$ electron density map of the linker segment contoured at 1.5 σ is shown in the enlarged box. In ePDZ-a, the missing residues for the linker segment are indicated with dashed lines. The concave surface around the linker area is highlighted in red circle. (c) Superposition of the two structures on the PDZ portion. ePDZ-b1 is colored as in (a); ePDZ-a is colored in light brown for PDZ and dark blue for FN3. The peptide was omitted for clarity. (d) Interactions of the FN3 loops with the PDZ/peptide complex in ePDZ-b1 (left panel) and ePDZ-a (right panel). The three FN3 loops (BC, DE and FG loops) are shown. The surface of the PDZ portion is shown in gray, and the peptide as yellow spheres. In the bottom panel, the surfaces of the PDZ and peptide portions in contact with the BC, DE and FG loops are shown in blue, cyan and red, respectively, and those in contact with both BC and FG loops are in magenta. The peptide surfaces without FN3 contact are shown in yellow, and the black lines enclose the bound peptide. The N- and C-termini of the peptide are also labeled.

Figure 4:
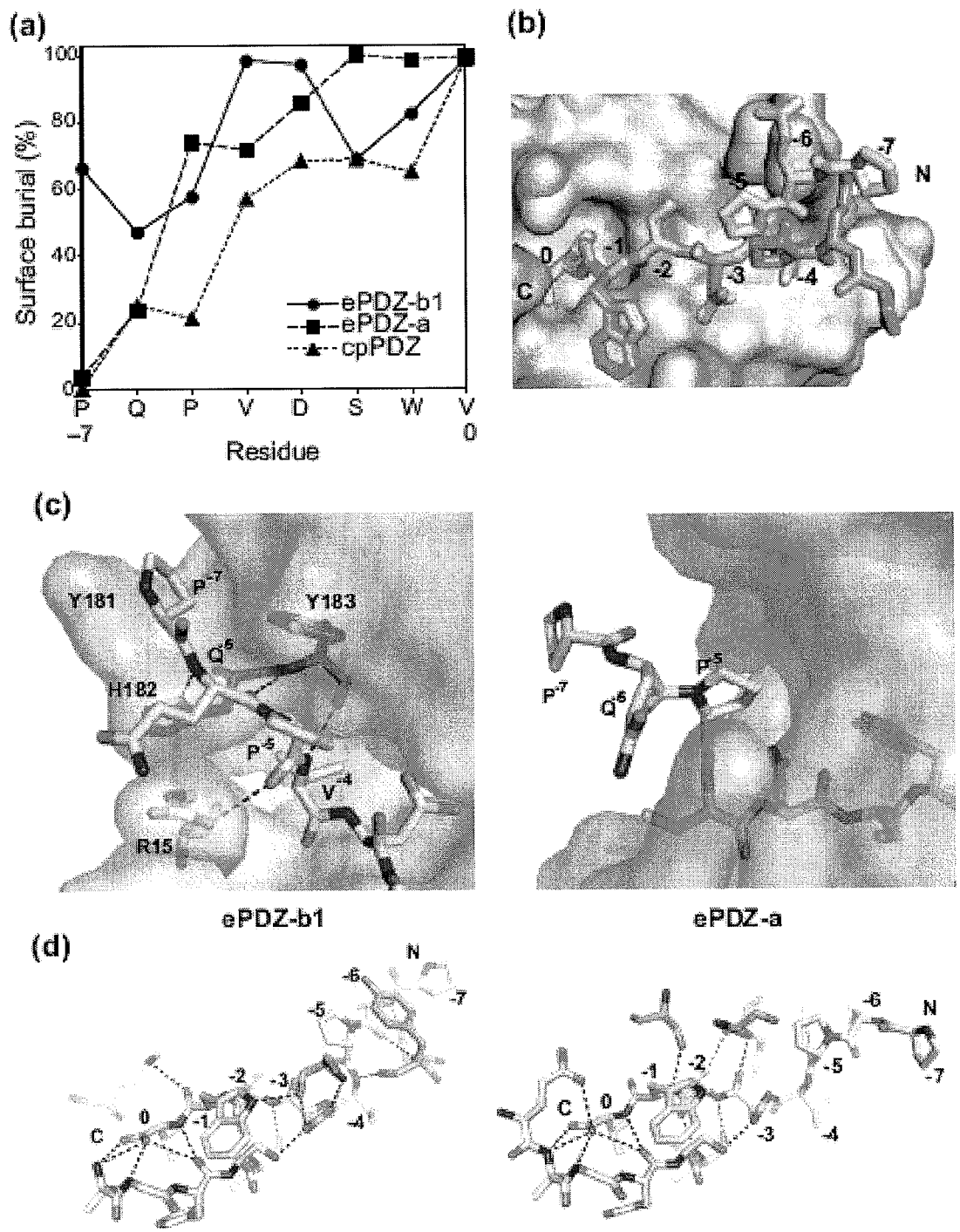

FIG. 4 illustrates interactions of ARVCF peptide with affinity clamps. (a) Surface burial of peptide residues by affinity clamps and Erbin PDZ. (b) Comparison of the peptide binding to the underlying PDZ domain. The ePDZ-a and ePDZ-b1 structures are superposed on the PDZ portion. The PDZ portion is shown in surface representation and the peptide is shown in stick. PDZ of ePDZ-b 1 is colored in gray and peptide in yellow; PDZ in ePDZ-a is colored in light brown and peptide in green. (c) Comparison of N-terminal three residues interacting with ePDZb1 (left panel) and ePDZ-a (right panel). The peptide and affinity clamps are colored as in FIG. 3. The orientation of the two structures are flipped by 180° to obtain a clear view of the N-terminal residues. Residues involved in H-bonds (dashed black lines) on the affinity clamps are shown in sticks with atomic coloring for nitrogen and oxygen. (d) A close view of H-bond pattern of the C-terminal five residues.

FIG. 5 illustrates a specificity profile of ePDZ-b family clamps. Amino acid sequences are shown for peptides selected from a phage-displayed peptide library sorted using ePDZ-b, ePDZb1 and ePDZ-b2. Results with the hepta-peptide library (a) and the penta-peptide library (b) are shown for each affinity clamp used. The number of occurrence of each sequence is also listed.

Figure 6:
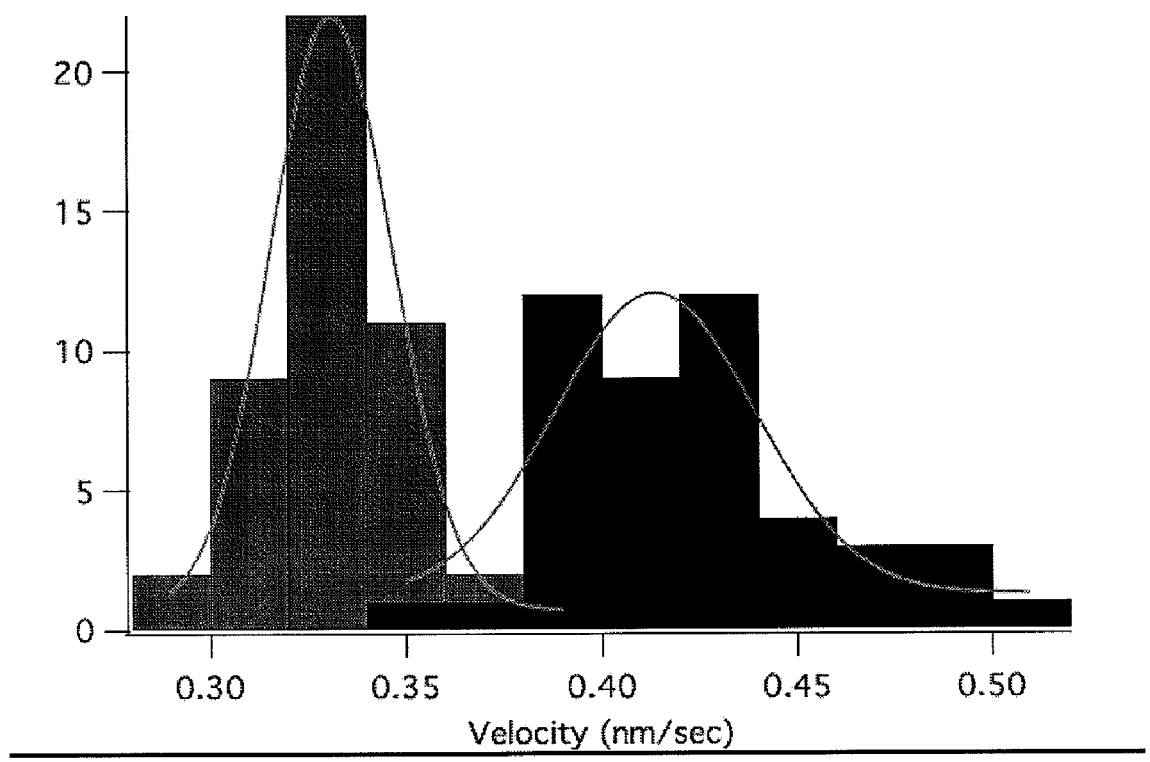

FIG. 6 shows filament gliding velocity histograms. The affinity clamp protein or anti-GFP antibody was immobilized on the coverslip surface then the tagged motor protein was allowed to bind. Filaments were introduced and bound to the motor protein without ATP. After motility solution with ATP was added the filaments moved along the surface. 45 filaments were analyzed for each regime by tracking filament ends as they moved. Data was plotted as a histogram and fit to a Gaussian distribution. Note that the data with the affinity clamp has a narrower distribution. This may be because the anti-GFP binds more weakly to the tagged protein bound to actin or the linkage and the presentation of the motor off the surface is more robust with the clamp. The difference in the absolute velocity may be due to different sample preparations and thus its significance needs to be confirmed.

Figure 7:
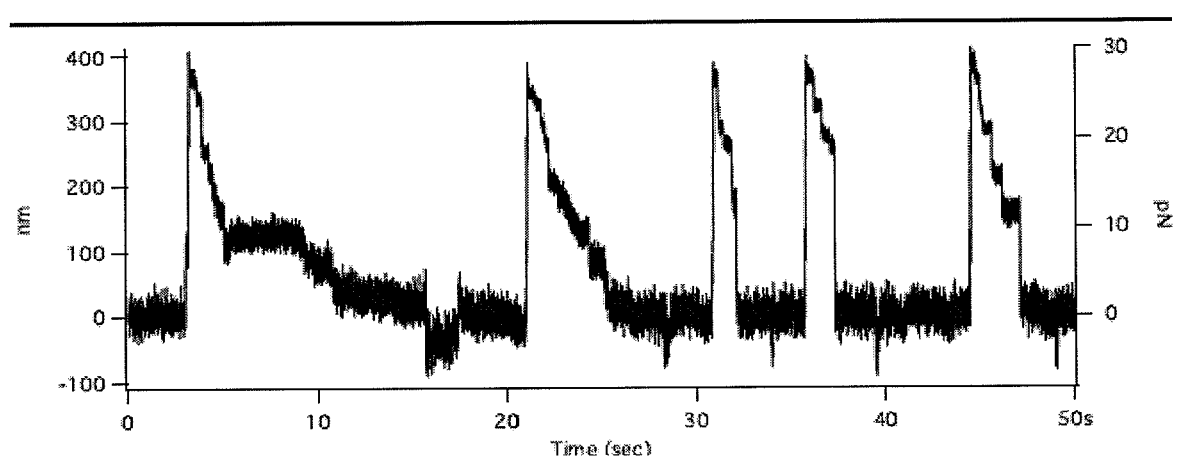

FIG. 7 shows the holding force in the trap. Single Myosin X motors with the affinity clamp recognition sequence were surface immobilized using the affinity clamp. An optically trapped actin dumb-bell was brought into proximity. As the motor interacted with the actin filament, the stage was jumped by approximately 300 nm displacing the dumb-bell out of the traps. This imposes a high force (~30 pN) on the actin-motor-affinity clamp complex. The motor then unbinds actin and the dumb-bell relaxes to the original position. Five such events are shown in the figure. The fact that the repetitive responses can be observed indicates that the affinity clamp-motor linkage remains intact after repeated applications of the high force.

Figure 8:
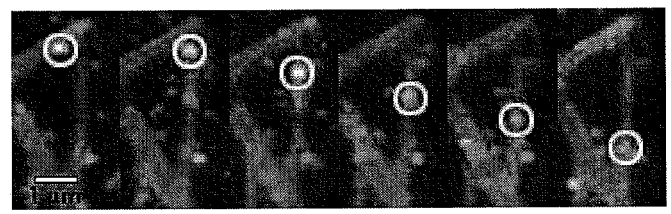

FIG. 8 illustrates TIRF sequence. The single cysteine of the clamp protein was conjugated to a Cy-5 dye via a maleimide linkage. Labeled clamp was mixed with a low dilution of motor and introduced to the experimental flow cell with fascin-actin bundled adhered to the surface via biotin/neutravidin. Single processive motor events were imaged by TIRF microscopy. One such event is represented here with a series of frames separated by 2 seconds. These results demonstrate the utility of the clamp-tag system for specific labeling.

Figure 9:
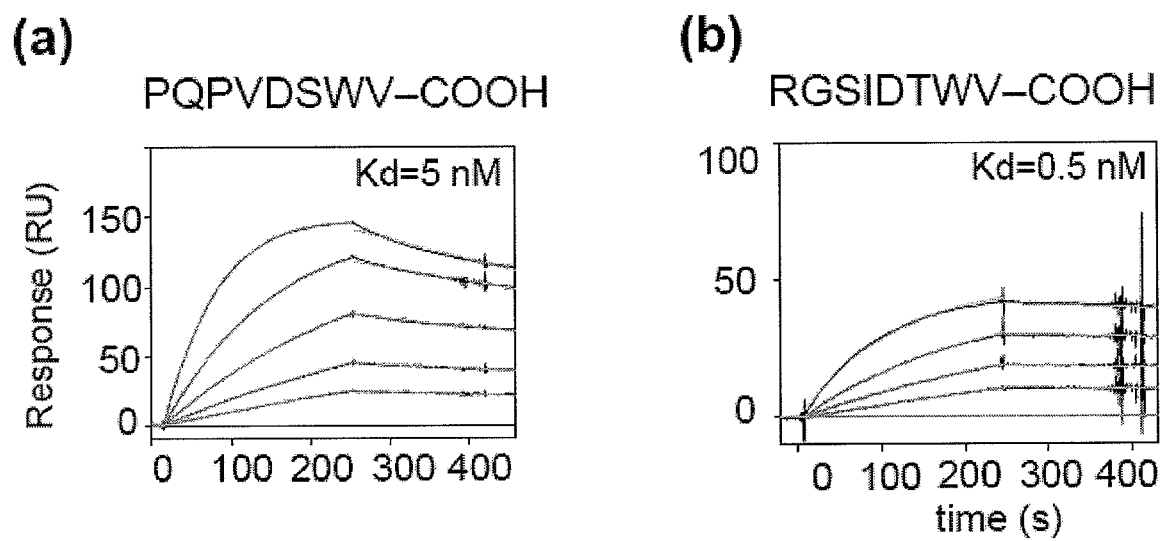

FIG. 9 shows the surface plasmon resonance analyses of the interactions between affinity clamps and peptide tags. The affinity clamps were immobilized and the target peptides in the form of yeast SUMO fusion protein were used as the analytes. (a) Sensorgrams for the interaction of the wild-type ARVCF peptide and ePDZ-b2. Data with 0, 10, 20, 40, 80 and 160 nM peptide are shown in black, and calculated curves from the global fittings of the 1:1 Langmuir binding model are in orange. The estimated dissociation constant is indicated.

The peptide sequence is also shown. (b) Sensorgrams for the interaction of the new tag peptide to ePDZ-b2. Data with 0, 10, 20, 40 and 80 nM target are shown. Note that the new tag peptide has higher affinity and that its dissociation rate is much slower than the original peptide.

DESCRIPTION

Peptide motifs are high-value targets for affinity reagents. Many natural domains are known to bind to such motifs. Although natural peptide-binding domains could be used directly as affinity reagents, their inherently low affinity makes it difficult to do so (they do work in a limited number of cases (Blagoev et al., 2003)). Natural peptide-binding domains have evolved to mediate signaling networks by reversibly and weakly binding to a specific peptide motif (Pawson and Nash, 2003). Thus, their sub-μM to low-μM Kd values are optimal for efficient information flow in signaling networks, but are much too weak to function as robust affinity reagents.

Embodiments of the invention include affinity clamps, affinity ligands, and methods of using and compositions comprising the affinity clamps and affinity ligands.

I. Affinity Ligands

Affinity ligands are peptides or peptide mimetics having 8, 9, 10, 11, 12, 13, 14, 15, 16, 17, 18, 19, 20, 25, 30 or more amino acid residues that can form an affinity ligand/affinity clamp complex having a dissociation constant of about, at least, or at most $1\times10^1$, $1\times10^{-1}$, $1\times10^{-2}$, $1\times10^{-3}$, $1\times10^{-4}$, $1\times10^{-5}$, $1\times10^{-6}$, $1\times10^{-7}$, $1\times10^{-8}$, $1\times10^{-9}$, $1\times10^{-10}$ μM, nM, or less. Typically, the affinity ligand will have a carboxyl terminus.

Affinity ligands can be coupled, either directly or indirectly to a target, e.g., a polypeptide, or molecule, or cell, or substrate, or other entity or moiety. Affinity ligands can be used to physically manipulate or detect a target. In certain aspects the affinity ligand is a peptide, and in particular a peptide having a carboxy terminus. The affinity ligand can be comprised in a fusion protein or coupled to a surface, e.g., a microparticle or cell surface.

Affinity clamps that bind the affinity ligands of the invention have a high affinity and low dissociation rate. The linkage between a tagged target and an affinity clamp do not break even under extreme conditions. When diluted down to single-molecule conditions (~10 pM) and well below the Kd of the clamp-ligand interaction (~500 pM), affinity ligand tagged targets remain attached to the clamp immobilized on a surface for hours of observation. The long retention time is far superior to that obtained with antibodies in comparable conditions. In one example, molecular motors immobilized through antibodies with only slightly higher Kds than a clamp-ligand system fall off within minutes, making it difficult to observe in single molecule conditions.

Affinity clamps that bind the affinity ligands of the invention can display a high specificity. Antibody preparations are often cross-reactive. Even when the antibody itself is not cross-reactive, commercial antibody preparations often contain cross-reacting contaminants. For example, recent commercial anti-GFP monoclonal antibodies bound to actin filaments and interfered with molecular motor assays. In contrast, minimal cross-reactivity has been observed for the affinity ligand clamp system in these same assays.

In certain aspects, the affinity ligand or affinity clamp conjugates are easy and convenient to make. The affinity clamp may be labeled through a unique Cys residue with a wide variety of probes (beads, fluorophors, quantum dots, nanogold particles) in a site-specific and stoichiometric manner. Such labeled clamps form a specific, quantitative 1:1 complex with the target protein. These probe systems can possess superior photochemistry compared to GFP. Also it is difficult to control chemical conjugation of monoclonal antibodies.

In still another aspect fluorescent affinity clamp conjugates have a reduced propensity to aggregate. To date, the inventors have not observed aggregation of fluorescently labeled clamps. In contrast, fluorescent antibodies tend to aggregate.

In yet another aspect, the clamp-ligand linkage can withstand high applied forces: motor-clamp complexes have been physically pulled and remained intact at forces >30 pN. This force is roughly 10× the stall force of the motor proteins studied (that is the maximal force needed to monitor in this type of experiment), or roughly half of the force needed to unfold a typical protein domain. Thus, the affinity ligand/clamp linkage is practically indestructible in the context of these or similar types of force measurements.

Furthermore, the affinity ligand/clamp system gives a non-compliant linkage: Unlike large antibodies, clamps are small (about one seventh the size of antibodies) and relatively inflexible proteins. Inflexibility is important for mechanical measurements such as those with molecular motors and the like. This feature also makes affinity clamps useful for precise positioning of proteins on engineered substrates.

In certain aspects the affinity ligand/clamp complex is relatively small: Unlike GFP (238 amino acids), the entire affinity ligand (minimum 8 residues) may be encoded within a single PCR primer. Also the small affinity ligand is unlikely to alter the properties of a protein to which it is attached.

Affinity ligands can also serve as a purification or isolation tag, which is discussed in more detail below.

Thus, some advantages include, but are not limited to easier and cheaper production of the affinity clamp. Its high expression level in *E. coli* makes it easy to achieve high purity. The affinity clamp can be easily modified by site-directed mutagenesis and by gene fusion providing for optimization of affinity ligand and affinity clamp characteristics. Additional advantages include affinity ligands that enable more effective and/or efficient methods of incorporating affinity tags.

Described herein are particular high affinity epitopes or tags or affinity ligands that can be identified by further characterization of the sequence specificity of an affinity clamp beyond the amino acid sequence utilized by the specificity domain of the affinity clamp. As an example, members of the ePDZ-b family were optimized at the positions beyond the C-terminal D(S/T)WV segment. Four ePDZ-b binding residues were fixed (DSWV (SEQ ID NO:7)) and the five preceding positions were diversified with all 20 amino acids. Specificity profiles produced with this library were similar for ePDZ-b family members (FIG. 2c and Supplementary FIG. 1b). The motif for ePDZ-b was X-8(R)-7(G/M)-6X-5(I/L/M)-4, that for ePDZ-b1 was X-8(R)-7(G/S/neutral)-6X-5(I/L/M)-4, and ePDZ-b2 showed further convergence at the −5 position to N and S. The number in the consensus sequence above represents the position and the letters in parenthesis represent the amino acid residues at that position (e.g., residue 8 is an arginine (R)). The patterns of the N-terminal three residues did not resemble the ARVCF sequence (PQPVD-SWV-COOH (SEQ ID NO:4)) to which the affinity clamps of interest were targeted, indicating that the affinity clamps could be further optimized to achieve higher binding affinity and possibly specificity. Indeed, a peptide designed to encode the most frequently observed amino acid at each position (RGSIDTWV-COOH (SEQ ID NO:1)) bound to ePDZ-b1 and ePDZ-b2 with eight-fold higher affinity relative to the ARVCF peptide. The dissociation half-life of the new peptide from ePDZ-b1 and ePDZ-b2 was about four hours. Compared with the binding motif of Erbin PDZ (ΦΦ(DE)(T/S)WV-COOH; Φ refers to a hydrophobic amino acid), the specificity profiles of ePDZ-b family were clearly more stringent and distinct at positions −4, −6 and −7, indicating that the domain interface evolution strategy can significantly expand the size of the recognition site beyond that of the capture domain.

In various aspects of the invention the RGSIDTWV-COOH (SEQ ID NO:1) epitope or affinity ligand, as well a variants thereof, are used as affinity ligands and can be used in combination with various ePDZ affinity clamps or other agents that specifically bind the RGSIDTWV-COOH (SEQ ID NO:1) ligand.

II. Capture Agents

As used herein, the term "capture agent" includes any agent which is capable of binding to an affinity ligand, as described herein, with at least detectable selectivity. A capture agent is capable of specifically interacting with (directly or indirectly), or binding to (directly or indirectly) an affinity ligand of the invention. The capture agent is preferably able to produce a signal that may be detected. In certain embodiments, the capture agent is an affinity clamp.

A. Affinity Clamps

The sequence specificity of affinity clamps were characterized and optimized. The optimized sequences were then adapted for use as affinity ligands. The sequence specificity of the ePDZ-b1 at the positions outside the C-terminal D(S/T)WV sequence were optimized by constructing a library having the C-terminal four residues fixed as DSWV and the five preceding positions diversified. Sorting of this library using ePDZ-b 1 resulted in sequence convergence to (R)(G/S/neutral)X(I/L/M)DSWV (SEQ ID NO:5), and sorting with ePDZ-b2 resulted in further conversion at the −4 position to (R)(G/S/neutral)(N/S) (I/L/M)DSWV (SEQ ID NO:6). These patterns closely resemble the ARVCF sequence. It is remarkable that ePDZ-b1 and ePDZ-b2 exhibit high binding specificity even at −7 position, indicating that the affinity clamping strategy can significantly expand the size of the binding domain relative to that of the original interaction domain, in this case, the PDZ domain.

Embodiments of the invention include methods of optimizing and designing an extended ligand (i.e., including additional amino acid residues to the epitope bound by a binding agent) that possesses improved binding affinity and/or specificity. In certain aspects an affinity clamp such as ePDZ-b 1 can be used to bind, detect, and/or purify the RGSIDTWV-COOH (SEQ ID NO:1) affinity ligand and as well as other targets coupled to the affinity ligand.

The architecture of an affinity clamp is modular with two modules or domains, each capable of binding a target motif. The first module or domain has a recognition domain that possesses inherent or natural specificity for the target motif. The second module or domain also has a recognition domain that binds the motif. The two modules are tethered together either directly (e.g., by a peptide or polypeptide sequence with the affinity clamp amino acid sequence (i.e., a fusion protein) coupled to two both domains), or indirectly (e.g., by a linker moiety or linker such as a synthetic polymer with reactive groups that can be coupled to each of the domains). In one aspect, the affinity clamp is a heterodimer of two monomers each having affinity for the target motif, the combination of which results in an increased affinity or specificity for a ligand. See PCT application PCT/US2008/083021, which is incorporated herein by reference in its entirety, for a detailed description of affinity clamps and related information.

ePDZ-a and ePDZ-b have a binding specificity to an ARVCF motif, wild-type erbin PDZ, and also bind to the C-terminus of δ-catenin with a low µM Kd. The erbin and δ-catenin sequences differ only at positions outside the core recognition motif, DSWV-COOH. The affinity enhancement of ePDZ-a was similar for both targets, erbin and δ-catenin. Remarkably, the ePDZ-b clone had very weak binding to δ-catenin, similar to the wild-type PDZ domain, showing that ePDZ-b discriminates between the two targets by ~200 fold. The ePDZ-b discriminates amino acids outside the DSWV-COOH motif shared by the two peptides, and thus, it expanded the size of the target motif. These results established that the affinity clamp technology can dramatically enhance both affinity and specificity of an interaction or specificity domain.

Two second-generation variants, ePDZ-b1 and ePDZ-b2, were prepared as protein samples and their binding properties were analyzed. The dissociation constants of the ePDZ-b1 and ePDZ-b2 for the AVFCF peptide were 5 and 4 nM, respectively, which were significantly smaller than the parent protein, ePDZ-b (56 nM) and represent 5,000-6,000-fold affinity enhancement relative to the original PDZ protein.

The affinity maturation process also dramatically enhanced the specificity of these affinity clamps. ePDZ-b1 and ePDZ-b2 can discriminate the AFVCF peptide (PQPVDSWV (SEQ ID NO:4)-COOH) and a homologous target from δ-catenin (PASPDSWV (SEQ ID NO:10)-COOH) by more than 2,000 fold, while the wild-type PDZ domain binds to them almost equally. Because the four C-terminal residues of the two peptides are identical, which are the primary recognition motif by the original PDZ domain, the stringent discrimination by these affinity clamps clearly indicates that the affinity clamp strategy can expand the size of recognition motif.

B. Other Capture Agents

Other capture agents include, but are not limited to an antibody or a fragment thereof (e.g., a single chain antibody), an RNA or DNA aptamer, an allosteric ribozyme, or a small molecule. Examples of capture agents are described in U.S. Patent Publication 20090023157, which is incorporated herein by reference in its entirety.

II. Polypeptide and Peptide Compositions

As used herein, a "protein" or "polypeptide" or "peptide" refers to a molecule comprising a sequence of amino acid residues. The terms described above may be used interchangeably. A "modified protein" or "modified polypeptide" or a "modified peptide" or a "variant" of the same refers to a protein or polypeptide or peptide whose chemical structure, particularly its amino acid sequence, is altered with respect to a reference protein or polypeptide or peptide. In some embodiments, a modified/variant protein or polypeptide has at least one modified activity or function (recognizing that proteins or polypeptides may have multiple activities or functions (e.g., a modified binding affinity or specificity)).

In certain embodiments the size of a protein or polypeptide or peptide may comprise, but is not limited to, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1100, 1200, 1300, 1400, 1500, 1750, 2000, 2250, 2500 residues or greater, and any range derivable therein, or derivative of a corresponding amino sequence described or referenced herein. It is contemplated that polypeptides or peptide may be altered by fusing or conjugating a heterologous protein sequence with a particular function.

As used herein, an "amino molecule" or "residue" refers to any amino acid, amino acid derivative, or amino acid mimic known in the art. In certain embodiments, the residues of the proteinaceous molecule are sequential, without any non-amino molecule interrupting the sequence of amino molecule residues. In other embodiments, the sequence may comprise one or more non-amino molecule moieties. In particular embodiments, the sequence of residues of the proteinaceous molecule may be interrupted by one or more non-amino molecule moieties.

Accordingly, the term "proteinaceous composition" encompasses amino molecule sequences comprising at least one of the 20 common amino acids in naturally synthesized proteins, or at least one modified or unusual amino acid.

Proteinaceous compositions may be made by any technique known to those of skill in the art, including (i) the expression of proteins, polypeptides, or peptides through standard molecular biological techniques, (ii) the isolation of proteinaceous compounds from natural sources, or (iii) the chemical synthesis of proteinaceous materials.

Amino acid sequence variants of an affinity ligand or affinity clamp and other polypeptides of the invention can be substitutional, insertional, or deletion variants. A variation in a polypeptide of the invention may affect 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more non-contiguous or contiguous amino acids of the polypeptide, as compared to reference sequence. A variant can comprise an amino acid sequence that is at least 50%, 60%, 70%, 80%, 90%, 95%, 98%, 99%, including all values and ranges there between, identical to any sequence provided or referenced herein. A variant can include 1, 2, 3, 4, 5, 6, 7, 8, 9, 10, 11, 12, 13, 14, 15, 16, 17, 18, 19, 20, or more substitute amino acids.

Deletion variants typically lack one or more residues of reference protein or peptide. Individual residues can be deleted or a number of contiguous amino acids can be deleted. A stop codon may be introduced (by substitution or insertion) into an encoding nucleic acid sequence to generate a truncated protein. Insertional mutants typically involve the addition of material at a non-terminal point in the polypeptide. This may include the insertion of one or more residues. Terminal additions, called fusion proteins, may also be generated. These fusion proteins include multimers or concatamers of one or more peptide or polypeptide described or referenced herein.

Substitutional variants typically contain the exchange of one amino acid for another at one or more sites within the protein or peptide, and may be designed to modulate one or more properties, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of the polypeptide is affected. Non-conservative changes typically involve substituting a residue with one that is chemically dissimilar, such as a polar or charged amino acid for a non-polar or uncharged amino acid, and vice versa.

Proteins of the invention may be recombinant, or synthesized in vitro. Alternatively, a non-recombinant or recombinant protein may be isolated from bacteria. It is also contemplated that a bacteria containing such a variant may be implemented in compositions and methods of the invention. Consequently, a protein need not be isolated.

The term "functionally equivalent codon" is used herein to refer to codons that encode the same amino acid, such as the six codons for arginine or serine, and also refers to codons that encode biologically equivalent amino acids (see Table below).

Codon Table

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

It also will be understood that amino acid and nucleic acid sequences may include additional residues, such as additional N- or C-terminal amino acids, or 5' or 3' sequences, respectively, and yet still be essentially as set forth in one of the sequences disclosed herein, so long as the sequence meets the criteria set forth above, including the maintenance of binding specificity or activity where protein expression is concerned. The addition of terminal sequences particularly applies to nucleic acid sequences that may, for example, include a nucleic acid sequence encoding an affinity ligand as described herein flanking either of the 5' or 3' portions of a heterologous coding region.

In certain aspects an affinity ligand can be included in a fusion protein or chimeric protein. The fusion protein can comprise a protease site N-terminal to the affinity ligand. The protease site can be used to remove the affinity ligand from the fusion protein. A number of protease sites are know in art. Also, other tags or ligands can be used in conjunction with affinity ligands described herein.

The present invention describes polypeptides, peptides, and proteins for use in various embodiments of the present invention. For example, specific polypeptides are assayed for or used to detect a target. Various peptides and proteins of the invention can be synthesized using automatic synthesizers that are commercially available and can be used in accordance with known protocols. See, for example, Stewart and Young, (1984); Tam et al., (1983); Merrifield, (1986); and Barany and Merrifield (1979), each incorporated herein by reference.

III. Nucleic Acids

In certain embodiments, the present invention concerns recombinant polynucleotides encoding the proteins, polypeptides, peptides incorporating an affinity ligand or subject to post expression coupling reactions to include an affinity ligand. The nucleic acid sequences for most proteins are included in the scope of the invention.

As used in this application, the term "polynucleotide" refers to a nucleic acid molecule that either is recombinant or has been isolated free of total genomic nucleic acid. Included within the term "polynucleotide" are oligonucleotides (nucleic acids of 100 residues or less in length), recombinant vectors, including, for example, plasmids, cosmids, phage, viruses, and the like. Polynucleotides include, in certain aspects, regulatory sequences, isolated substantially away from their naturally occurring genes or protein encoding sequences. Polynucleotides may be single-stranded (coding or antisense) or double-stranded, and may be RNA, DNA (genomic, cDNA or synthetic), analogs thereof, or a combination thereof. Additional coding or non-coding sequences may, but need not, be present within a polynucleotide.

In this respect, the term "gene," "polynucleotide," or "nucleic acid" is used to refer to a nucleic acid that encodes a protein, polypeptide, or peptide (including any sequences required for proper transcription, post-translational modification, or localization). As will be understood by those in the art, this term can encompass genomic sequences, expression cassettes, cDNA sequences, and smaller engineered nucleic acid segments that express, or may be adapted to express, proteins, polypeptides, domains, peptides, fusion proteins, and mutants. A nucleic acid encoding all or part of a polypeptide may contain a contiguous nucleic acid sequence of: 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1095, 1100, 1500, 2000, 2500, 3000, 3500, 4000, 4500, 5000, 5500, 6000, 6500, 7000, 7500, 8000, 9000, 10000, or more nucleotides, nucleosides, or base pairs, including all values and ranges therebetween, of a polynucleotide encoding one or more amino acid sequence described or referenced herein. It also is contemplated that a particular polypeptide may be encoded by nucleic acids containing variations having slightly different nucleic acid sequences but, nonetheless, encode the same or substantially similar protein.

In particular embodiments, the invention concerns isolated nucleic acid segments and recombinant vectors incorporating nucleic acid sequences that encode an affinity ligand having the sequence of SEQ ID NO:1. The term "recombinant" may be used in conjunction with a polynucleotide or polypeptide and generally refers to a polypeptide or polynucleotide produced and/or manipulated in vitro or that is a replication product of such a molecule.

In other embodiments, the invention concerns isolated nucleic acid segments and recombinant vectors incorporating nucleic acid sequences that encode an affinity ligand and/or an affinity clamp.

The nucleic acid segments used in the present invention can be combined with other nucleic acid sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant nucleic acid protocol. In some cases, a nucleic acid sequence may encode a polypeptide sequence with additional heterologous coding sequences, for example to allow for purification of the polypeptide, transport, secretion, post-translational modification, or for therapeutic benefits such as targeting or efficacy. As discussed above, an affinity ligand and/or other heterologous polypeptide may be added to the modified polypeptide-encoding sequence, wherein "heterologous" refers to a polypeptide that is not the same as the modified polypeptide.

In certain embodiments, the present invention provides polynucleotide variants having substantial identity to the sequences disclosed herein; those comprising at least 70%, 75%, 80%, 85%, 90%, 95%, 96%, 97%, 98%, or 99% or higher sequence identity, including all values and ranges there between, compared to a polynucleotide sequence of this invention using known methods (e.g., BLAST analysis using standard parameters).

The invention also contemplates the use of polynucleotides which are complementary to all the above described polynucleotides.

Alternatively, recombinant DNA technology may be employed wherein a nucleotide sequence which encodes an affinity ligand of the invention is in an expression vector, transformed or transfected into an appropriate host cell and cultivated under conditions suitable for expression.

One embodiment of the invention includes the use of recombinant expression in a host cell, including microorganisms, for the production and/or presentation of polypeptides or peptides comprising the affinity ligand. The gene for the polypeptide or peptide of interest may be transferred into appropriate host cells followed by culture of cells under the appropriate conditions. The generation of recombinant expression vectors, and nucleic acid sequence encoding an affinity ligand as well as other elements is well known in the art and briefly discussed herein. Alternatively, the protein to be produced may be an endogenous protein normally synthesized by the cell that is isolated and purified and then coupled to an affinity ligand.

A. Vectors

Polypeptides of the invention may be encoded by a nucleic acid molecule comprised in a vector. The term "vector" is used to refer to a carrier nucleic acid molecule into which a heterologous nucleic acid sequence can be inserted for introduction into a cell where it can be replicated and expressed. A nucleic acid sequence can be "heterologous," which means that it is in a context foreign to the cell in which the vector is being introduced or to the nucleic acid in which is incorporated, which includes a sequence homologous to a sequence in the cell or nucleic acid but in a position within the host cell or nucleic acid where it is ordinarily not found. Vectors include DNAs, RNAs, plasmids, cosmids, viruses (bacteriophage, animal viruses, and plant viruses), and artificial chromosomes (e.g., YACs). One of skill in the art would be well equipped to construct a vector through standard recombinant techniques (for example Sambrook et al., 2001; Ausubel et al., 1996, both incorporated herein by reference).

The term "expression vector" refers to a vector containing a nucleic acid sequence coding for at least part of a gene product capable of being transcribed. In some cases, RNA molecules are then translated into a protein, polypeptide, or peptide. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described herein.

1. Promoters and Enhancers

A "promoter" is a control sequence. The promoter is typically a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and expression of that sequence. A promoter may or may not be used in conjunction with an "enhancer," which refers to a cis-acting regulatory sequence involved in the transcriptional activation of a nucleic acid sequence.

Naturally, it may be important to employ a promoter and/or enhancer that effectively directs the expression of the DNA segment in the cell type or organism chosen for expression. Those of skill in the art of molecular biology generally know the use of promoters, enhancers, and cell type combinations for protein expression (see Sambrook et al., 2001, incorporated herein by reference). The promoters employed may be constitutive, tissue-specific, or inducible and in certain embodiments may direct high level expression of the introduced DNA segment under specified conditions, such as large-scale production of recombinant proteins or peptides.

Various elements/promoters may be employed in the context of the present invention to regulate the expression of a gene. Examples of such inducible elements, which are regions of a nucleic acid sequence that can be activated in response to a specific stimulus, include but are not limited to Immunoglobulin Heavy Chain (Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990), Immunoglobulin Light Chain (Queen et al., 1983; Picard et al., 1984), T Cell Receptor (Luria et al., 1987; Winoto et al., 1989; Redondo et al.; 1990), HLA DQ α and/or DQ β (Sullivan et al., 1987), β Interferon (Goodbourn et al., 1986; Fujita et al., 1987; Goodbourn et al., 1988), Interleukin-2 (Greene et al., 1989), Interleukin-2 Receptor (Greene et al., 1989; Lin et al., 1990), MHC Class II 5 (Koch et al., 1989), MHC Class II HLA-DRα (Sherman et al., 1989), β-Actin (Kawamoto et al., 1988; Ng et al.; 1989), Muscle Creatine Kinase (MCK) (Jaynes et al., 1988; Horlick et al., 1989; Johnson et al., 1989), Prealbumin (Transthyretin) (Costa et al., 1988), Elastase I (Ornitz et al., 1987), Metallothionein (MTII) (Karin et al., 1987; Culotta et al., 1989), Collagenase (Pinkert et al., 1987; Angel et al., 1987), Albumin (Pinkert et al., 1987; Tronche et al., 1989, 1990), α-Fetoprotein (Godbout et al., 1988; Campere et al., 1989), γ-Globin (Bodine et al., 1987; Perez-Stable et al., 1990), β-Globin (Trudel et al., 1987), c-fos (Cohen et al., 1987), c-Ha-Ras (Triesman, 1986; Deschamps et al., 1985), Insulin (Edlund et al., 1985), Neural Cell Adhesion Molecule (NCAM) (Hirsh et al., 1990), α1-Antitrypain (Latimer et al., 1990), H2B (TH2B) Histone (Hwang et al., 1990), Mouse and/or Type I Collagen (Ripe et al., 1989), Glucose-Regulated Proteins (GRP94 and GRP78) (Chang et al., 1989), Rat Growth Hormone (Larsen et al., 1986), Human Serum Amyloid A (SAA) (Edbrooke et al., 1989), Troponin I (TN I) (Yutzey et al., 1989), Platelet-Derived Growth Factor (PDGF) (Pech et al., 1989), Duchenne Muscular Dystrophy (Klamut et al., 1990), SV40 (Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988), Polyoma (Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell et al., 1988), Retroviruses (Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Choi et al., 1988; Reisman et al., 1989), Papilloma Virus (Campo et al., 1983; Lusky et al., 1983; Spandidos and Wilkie, 1983; Spalholz et al., 1985; Lusky et al., 1986; Cripe et al., 1987; Gloss et al., 1987; Hirochika et al., 1987; Stephens et al., 1987), Hepatitis B Virus (Bulla et al., 1986; Jameel et al., 1986; Shaul et al., 1987; Spandau et al., 1988; Vannice et al., 1988), Human Immunodeficiency Virus (Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989), Cytomegalovirus (CMV) IE (Weber et al., 1984; Boshart et al., 1985; Foecking et al., 1986), Gibbon Ape Leukemia Virus (Holbrook et al., 1987; Quinn et al., 1989).

Inducible elements include, but are not limited to MT II-Phorbol Ester (TFA)/Heavy metals (Palmiter et al., 1982; Haslinger et al., 1985; Searle et al., 1985; Stuart et al., 1985; Imagawa et al., 1987, Karin et al., 1987; Angel et al., 1987b; McNeall et al., 1989); MMTV (mouse mammary tumor virus)-Glucocorticoids (Huang et al., 1981; Lee et al., 1981; Majors et al., 1983; Chandler et al., 1983; Lee et al., 1984; Ponta et al., 1985; Sakai et al., 1988); (β-Interferon-poly(rI) x/poly(rc) (Tavernier et al., 1983); Adenovirus 5 E2-E1A (Imperiale et al., 1984); Collagenase-Phorbol Ester (TPA) (Angel et al., 1987a); Stromelysin-Phorbol Ester (TPA) (Angel et al., 1987b); SV40-Phorbol Ester (TPA) (Angel et al., 1987b); Murine MX Gene-Interferon, Newcastle Disease Virus (Hug et al., 1988); GRP78 Gene-A23187 (Resendez et al., 1988); α-2-Macroglobulin-IL-6 (Kunz et al., 1989); Vimentin-Serum (Rittling et al., 1989); MHC Class I Gene H-2κb-Interferon (Blanar et al., 1989); HSP70-E1A/SV40 Large T Antigen (Taylor et al., 1989, 1990a, 1990b); Proliferin-Phorbol Ester/TPA (Mordacq et al., 1989); Tumor Necrosis Factor-PMA (Hensel et al., 1989); and Thyroid Stimulating Hormone α Gene-Thyroid Hormone (Chatterjee et al., 1989).

The particular promoter that is employed to control the expression of peptides or proteins encoding polynucleotides of the invention is not believed to be critical, so long as it is capable of expressing the polynucleotide in a targeted cell, such as a bacterial cell. Where a human cell is targeted, it is preferable to position the polynucleotide coding region adjacent to and under the control of a promoter that is capable of being expressed in a human cell. Generally speaking, such a promoter might include either a bacterial, human or viral promoter.

2. Initiation Signals and Internal Ribosome Binding Sites (IRES)

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. In certain embodiments of the invention, the use of internal ribosome entry sites (IRES) elements are used to create multigene, or polycistronic, messages.

3. Selectable and Screenable Markers

In certain embodiments of the invention, cells containing a nucleic acid construct of the present invention may be identified in vitro or in vivo by encoding a screenable or selectable marker in the expression vector. When transcribed and translated, a marker confers an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

B. Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector or expressing a heterologous gene encoded by a vector. A host cell can, and has been, used as a recipient for vectors or viruses. A host cell may be "transfected" or "transformed," which refers to a process by which exogenous nucleic acid, such as a recombinant protein-encoding sequence, is transferred or introduced into the host cell. A transformed cell includes the primary subject cell and its progeny.

Host cells may be derived from prokaryotes or eukaryotes, including bacteria, yeast cells, insect cells, and mammalian cells for replication of the vector or expression of part or all of the nucleic acid sequence(s). Numerous cell lines and cultures are available for use as a host cell, and they can be obtained through the American Type Culture Collection (ATCC), which is an organization that serves as an archive for living cultures and genetic materials (www.atcc.org). Examples of mammalian host cell lines include, but are not limited to Vero and HeLa cells, B- and T-cell lines, such as CEM, 721.221, H9, Jurkat, Raji, as well as cell lines of Chinese hamster ovary, W138, BHK, COS-7, 293, HepG2, 3T3, RIN and MDCK cells. In addition, a host cell strain may be chosen that modulates the expression of the inserted sequences, or that modifies and processes the gene product in the manner desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to ensure the correct modification and processing of the foreign protein expressed.

A number of selection systems may be used including, but not limited to HSV thymidine kinase, hypoxanthine-guanine phosphoribosyltransferase, and adenine phosphoribosyltransferase genes, in tk–, hgprt– or aprt– cells, respectively. Also, anti-metabolite resistance can be used as the basis of selection: for dhfr, which confers resistance to trimethoprim and methotrexate; gpt, which confers resistance to mycophenolic acid; neo, which confers resistance to the aminoglycoside G418; and hygro, which confers resistance to hygromycin.

Animal cells can be propagated in vitro in two modes: as non-anchorage-dependent cells growing in suspension throughout the bulk of the culture or as anchorage-dependent cells requiring attachment to a solid substrate for their propagation (i.e., a monolayer type of cell growth).

C. Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

In addition to the disclosed expression systems of the invention, other examples of expression systems include STRATAGENE®'s COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

IV. Methods of Using Affinity Ligands

With recombinant DNA methods it is possible to create fusion proteins consisting of a protein to be studied and various tags used for detection and purification. Furthermore, affinity ligands of the invention can be coupled to various targets by coupling or conjugation chemistries that are well known in the art.

Affinity ligands have been used for the generation of purified fusion proteins in a multitude of applications, including structural genomics, antibody generation, and interaction analysis. Affinity ligands can be used in various methods and techniques including, but not limited to affinity capture, detection, conjugation, and/or detection/quantification. The detection/quantification applications can be based on FRET labeled clamps or FRET labeled affinity ligand/affinity clamp pairs.

A "capture agent" is a generic term for a complementary partner in an affinity binding pair and is generally used to capture a ligand or hapten by binding it. Affinity binding pairs include an affinity clamp:affintity ligands pair.

Assay formats including, but not limited to microfluidic devices, laminar flow, lateral flow, capillary, dipstick, multi-well plate, and test tube formats are contemplated.

A. Detection and/or Quantification

Means for detecting, as used herein, refers to an apparatus for displaying an endpoint, i.e., the result of an assay, and may include a detection channel and/or a sensor and evaluation of a detection endpoint. Detection endpoints are evaluated by an observer visually, or by a machine equipped with a spectrophotometer, fluorometer, luminometer, photomultiplier tube, photodiode, nephlometer, photon counter, voltmeter, ammeter, pH meter, capacitative sensor, radio-frequency transmitter, magnetoresistometer, or Hall-effect device. Particles, beads and microspheres having impregnated color or having a higher diffraction index may be used to facilitate visual or machine-enhanced detection of an assay endpoint. Magnifying lenses in the cover plate, optical filters, colored fluids and labeling may be used to improve detection and interpretation of assay results.

Detection of affinity ligands and/or affinity clamps may include coupled, conjugated, embedded, or coated "labels" such as, but not limited to, dyes such as chromophores and fluorophores, for example Texas Red; radio frequency tags, plasmon resonance, spintronic, radiolabel, Raman scattering, chemoluminescence, or inductive moment as are known in the prior art. QDots, such as CdSe coated with ZnS, decorated on magnetic beads, or amalgamations of QDots and paramagnetic $Fe_3O_4$ microparticles, can be used to label an affinity ligand or an affinity clamp.

Fluorescence quenching detection endpoints are also anticipated. A variety of substrate and product chromophores associated with enzyme-linked immunoassays are also well known in the art and provide a means for amplifying a detection signal so as to improve the sensitivity of the assay. Detection systems are optionally qualitative, quantitative or semi-quantitative. Visual detection is preferred for its simplicity, however detection can involve visual detection, machine detection, manual detection or automated detection.

In general, the different conformational states of the affinity clamps and/or the affinity ligand used in accordance with the invention will correspond to different separation distances between the first and second domains, whereby changes in conformation may be conveniently monitored by means of a separation sensitive signal.

Various forms of separation sensitive signal systems may be used with the affinity clamps of the invention. In such embodiments, a first domain includes a first signaling moiety and a second domain or affinity ligand includes a second signaling moiety, and the first and second signaling moieties are capable of interacting to produce a detectable signal. The signaling moieties may include dyes, quenchers, reporter proteins and quantum dots. Particularly useful are embodiments in which the biorecognition modules include optical signaling pairs that can produce a detectable signal when the proximity of the domains or the ligand/clamp with respect to each other changes with the binding of affinity ligand. Suitably, the first and second signaling moieties are a fluorescence resonance energy (FRET) donor group and a receptor group, respectively. The change in proximity of the FRET groups produces an optical signal which differs between when binding is and is not present.

It will also be appreciated that various other means may be used for "reading" the presence of an affinity ligand binding to an affinity clamp, and/or the resultant change in conformational state of the affinity clamp structure or the affinity ligand/clamp complex. Many different labeling systems may be used, such as fluorophore labeling (including quantum dot), radio-labeling, and redox labeling.

B. Affinity Capture

Capture or immobilization refers to the use of affinity binding pairs to concentrate an analyte or detection complex. Concentration can be on a solid phase surface, particle, or porous adsorbent material, generally so that the analyte can be detected, concentrated or purified. Solid phase capture may be achieved with capture agents such as immobilized affinity clamp.

1. Chromatography

The use of affinity for purification of proteins through chromatography relies on the use of an affinity ligand and/or affinity clamp coupled to a matrix to allow specific capture of the product from a complex mixture. In this way, an essentially pure product can be obtained with a single operation. Most monoclonal antibodies used for research and diagnostics and essentially all therapeutic antibodies used to treat patients have been purified using affinity chromatography. Recently, protein engineering and design have been used to create new affinity reagents more suitable for affinity chromatography, as exemplified by the affinity ligand of the present invention. Affinity ligands described herein can be coupled to a protein of interest prior to, during or after production and purified or isolated using the methods of the current invention.

The preparation of a chemically and functionally homogenous sample is a fundamental step in biochemical and biophysical characterization of proteins. Among the purification methods available, affinity chromatography is a preferred method due to its high specificity and capacity. Due to their high affinity, high specificity and low dissociation constants, the affinity clamps in accordance with the invention are well suited for use as immobilized affinity reagents for use in affinity chromatography. Affinity clamps can be immobilized on a solid substrate and used to purify a protein of interest by affinity chromatography. An affinity ligand for which an affinity clamp is available can be fused to a protein of interest using recombinant techniques. This fusion peptide can then be purified by affinity chromatography by virtue of the binding of the affinity ligand to immobilized affinity clamps.

Compositions of the invention can be used in various chromatographic compositions and methods. Samples can be fractionated by a number of known fractionation techniques utilizing the compositions described herein. Since such fractionation methods separate molecules, such techniques are used to resolve sample molecules. Methods for resolving sample steps that are well known to those skilled in the art. Chromatographic techniques include, but are not limited to affinity chromatography.

2. Precipitation

Another application of affinity ligand is the technique most commonly called immunoprecipitation, which is based on the use of a specific binding moiety (e.g., an affinity clamp) coupled to a solid matrix to capture the protein or other targets comprising an epitope or affinity ligand that is bound by the specific binding moiety. This technique is used in a number of applications such as molecular profiling of protein modifications to pathway mapping and network analysis.

3. Protein-Protein Interaction

Protein-protein interactions are important and there are various methods used to detect them. The affinity ligand/ affinity clamp pairs can be adapted to provide affinity and specificity of interaction in a number of protein-protein or protein-ligand interaction studies.

Co-immunoprecipitation is considered to be the gold standard assay for studying protein-protein interactions. The protein of interest is isolated with a specific binding agent, e.g., an affinity clamp. Interaction partners which stick to or interact directly or indirectly with the isolated protein can be subsequently identified. Positive results may indicate that two proteins interact directly or may interact via a bridging protein. Pull-down assays are a common variation of immunoprecipitation and can be used in screening for interacting proteins.

Tandem affinity purification (TAP) method allows high throughput identification of protein interactions. TAP involves creating a fusion protein with a designed piece, the affinity ligand, on the end. The protein of interest with the affinity ligand first binds to a substrate, the affinity ligand is then dissociated and a different segment of the affinity ligand binds reversibly to different surface. After the protein of interest has been washed through two affinity columns, it can be examined for binding partners.

Chemical crosslinking is often used to "fix" protein interactions in place before trying to isolate/identify interacting proteins. Common crosslinkers for this application include the non-cleavable NHS-ester crosslinker, bis-sulfosuccinimidyl suberate (BS3); a cleavable version of BS3, dithiobis (sulfosuccinimidyl propionate) (DTSSP); and the imidoester crosslinker dimethyl dithiobispropionimidate (DTBP) that is popular for fixing interactions in ChIP assays.

4. Substrates

In certain embodiments, the capture agents are immobilized, permanently or reversibly, on a solid support such as a bead, chip, or slide. When employed to analyze a complex mixture of proteins, the immobilized capture agent can be arrayed and/or otherwise labeled for deconvolution of the binding data to yield identity of the capture agent (and therefore of the protein to which it binds) and (optionally) to quantitate binding. Affinity ligands or affinity clamps can be coupled to a substrate. Substrates include various microparticle and surfaces.

In certain aspects the particle can be a "nanoparticle", "bead", or "microsphere", or by other terms as known in the art, having at least one dimension, such as apparent diameter or circumference, in the micron or nanometer range. Such particles may be composed of, contain cores of, or contain granular domains of a paramagnetic or superparamagnetic material, such as the $Fe_2O_3$ and $Fe_3O_4$ ($\alpha$-Fe crystal type), $\alpha'$-FeCo, $\epsilon$-Cobalt, CoPt, $CrPt_3$, $SmCO_5$, Nickel and nickel alloys, $Cu_2MnAl$, $\alpha$-FeZr, $Nd_2Fe_{14}B$, NoTi, for example. In certain aspects these particles are "superparamagnetic", meaning that they are attracted to a magnetic field but retain no residual magnetism after the field is removed. Therefore, suspended superparamagnetic particles coupled to a target of interest can be removed from a matrix using a magnetic field, but they do not agglomerate (i.e., they stay suspended) after removal of the field. Particles can be composite materials with RF-tags, QDots, up-converting fluorophores, colloid sols and clays, and the like are contemplated. Particles may have chromogenic properties, or may be combined with other colloidal metal particles with chromogenic properties.

The surface of a substrate may be modified by adsorption or covalent attachment of an affinity ligand and/or an affinity clamp.

C. Affinity Assays

An Enzyme-Linked Immunosorbent Assay (ELISA) may also be used for detection of an affinity ligand that interacts with a capture agent. In an ELISA, the indicator molecule is covalently coupled to an enzyme and may be quantified by determining with a spectrophotometer the initial rate at which the enzyme converts a clear substrate to a correlated product. Methods for performing ELISA are well known in the art and described in, for example, Perlmann and Perlmann (1994); Crowther (1995); and Harlow and Lane (1988), the contents of each of which are incorporated by reference. Sandwich (capture) ELISA may also be used to detect an affinity ligand that interacts with two capture agents. Sandwich ELISAs for the quantitation of targets of interest are especially valuable when the concentration of the target in the sample is low and/or the target of interest is present in a sample that contains high concentrations of contamination.

D. Biosensors

Affinity clamps in accordance with the invention may be suitably used as a biosensor wherein the first and second biorecognition modules are each labeled with paired signaling moieties as described above.

A plurality of affinity clamps can be immobilized, directly or indirectly to a support or substrate to form an array of clamps or an array of biosensors. Supports or substrates can take a variety of forms such as polymers, glasses, metal and those with coating therein. Arrays are ordered arrangements of elements, allowing them to be displayed and examined in parallel. Arrays of immobilized affinity clamps can be used to detect affinity ligand coupled to various components and demonstrate or study the binding reaction of a target. Certain array formats are sometimes referred to as "biochips." Biochips may include a plurality of locations configured so that each location is spatially addressable. Typically, the clamp format is configured in a row and column format with regular spacing between locations, wherein each location has machine-readable (e.g., computer-readable) information to identify the location on the surface of the substrate.

In several other embodiments, detection of the presence of an affinity ligand that interacts with a capture agent may be achieved without labeling. For example, determining the ability of an affinity ligand to bind to a capture agent can be accomplished using a technology such as real-time Biomolecular Interaction Analysis (BIA). Sjolander and Urbaniczky (1991) and Szabo et al. (1995). As used herein, "BIA" is a technology for studying biospecific interactions in real time, without labeling any of the interactants (e.g., BIAcore). Determining the ability of an affinity ligand to bind to a capture agent can also be accomplished using technologies such as surface-enhanced laser desorption/ionization time-of-flight mass spectrometry (SELDI-TOF) and self-assembled monolayers for matrix assisted laser desorption ionization mass spectrometry. Poon (2007) and Mrksich (2008).

E. Conjugation

Conjugation is the process of coupling two molecules together in a covalent or non-covalent linkage. The product of a conjugation reaction is a conjugate. Examples of conjugates include protein-protein conjugates, peptide-nucleic acid conjugates, peptide-drug conjugates. Conjugates of the invention can include a first moiety coupled to an affinity ligand and a second moiety coupled to an affinity clamp, thus when in proximity the first moiety is conjugated to the second via the affinity ligand/clamp interaction. Additional examples of conjugates can be found in U.S. Publications 20030143598, 20030175702, and 20080050731.

V. Detection

The affinity ligands and/or capture agents of the present invention may be modified to enable detection using techniques known to one of ordinary skill in the art, such as fluorescent, radioactive, chromatic, optical, and other physical or chemical labels, as described herein below. In one embodiment, the affinity ligand and/or affinity clamp is or are conjugated with a reporter molecule such as a fluorescent molecule or an enzyme, and used to detect the presence of bound target on a substrate (such as a chip or bead), in for example, a "sandwich" type assay in which one capture agent is immobilized on a support to capture a target, while a second, labeled capture agent also specific for the captured target may be added to detect/quantitate the captured target.

A. Labels

The affinity ligands and affinity clamps of the invention, as well as compositions, e.g., microarrays or beads, comprising such have a wide range of applications in the health care industry, e.g., in therapy, in clinical diagnostics, in in vivo imaging or in drug discovery.

To detect the interaction of an affinity ligand/clamp, a variety of known methods can be modified and used with the current compositions. The affinity ligand and/or clamp may be labeled with a detectable label, and the amount of bound label directly measured. The term "label" is used herein in a broad sense to refer to agents that are capable of providing a detectable signal, either directly or through interaction with one or more additional members of a signal producing system. Labels that are directly detectable and may find use in the present invention include, for example, fluorescent labels such as fluorescein, rhodamine, BODIPY, cyanine dyes (e.g., from Amersham Pharmacia), Alexa dyes (e.g., from Molecular Probes, Inc.), fluorescent dye phosphoramidites, beads, chemiluminescent compounds, colloidal particles, and the like. Suitable fluorescent dyes are known in the art, including fluoresceinisothiocyanate (FITC); rhodamine and rhodamine derivatives; Texas Red; phycoerythrin; allophycocyanin; 6-carboxyfluorescein (6-FAM); 2',7'-dimethoxy-41,51-dichloro carboxyfluorescein (JOE); 6-carboxy-X-rhodamine (ROX); 6-carboxy-21,41,71,4,7-hexachlorofluorescein (HEX); 5-carboxyfluorescein (5-FAM); N,N,N1,N'-tetramethyl carboxyrhodamine (TAMRA); sulfonated rhodamine; Cy3; Cy5; etc. Radioactive isotopes, such as $^{32}P$, $^{3}H$, $^{25}I$, and the like can also be used for labeling. In addition, labels may also include near-infrared dyes (Wang et al., 2000), upconverting phosphors (Hampl et al., 2001), DNA dendrimers (Stears et al., 2000), quantum dots (Bruchez et al., 1998), latex beads (Okana et al., 1992), selenium particles (Stimpson et al., 1995), and europium nanoparticles (Harma et al., 2001). The label is one that preferably does not provide a variable signal, but instead provides a constant and reproducible signal over a given period of time.

All the above named reagents may be used to label the affinity ligands and/or affinity clamps. The label may also be a covalently bound enzyme capable of providing a detectable product signal after addition of suitable substrate. Examples of suitable enzymes for use in the present invention include horseradish peroxidase, alkaline phosphatase, malate dehydrogenase and the like.

B. Combination Tagging

In certain aspects more that one tag will be incorporated into or coupled with a target. A target can contain two unique, non-overlapping tags, one recognized by the capture agent (affinity ligand recognized by the affinity clamp), the other recognized by a second detection or capture agent. In a related embodiment, the affinity ligand in a combination tag can be used to specifically label a particular subset of targets or as a general label for a set of targets with specific targets labeled by one or more second tag. The spatial arrangement of these two tags is such that binding by one will not substantially affect the binding by the other. In addition, the length of the peptide fragment is such that it encompasses two tags properly spaced from each other.

VI. Affinity Ligand/Clamp Kits

Any of the compositions described herein may be comprised in a kit. In a non-limiting example, reagents for cloning nucleic acids, labeling peptides, and/or evaluating affinity ligand/clamp interaction can be included in a kit. The kit may further include reagents for creating or synthesizing affinity ligand tagged targets. The kits will thus comprise, in suitable container means, a nucleic acid or nucleic acid vector encoding an affinity ligand or affinity clamp that are subsequently used to produce a tagged target or a binding agent. In other aspects, the kit may include various supports, such as glass, nylon, polymeric beads, and the like, and/or reagents for coupling an affinity ligand and/or affinity clamp to a substrate or support. It may also include one or more buffers, such as reaction buffer, labeling buffer, washing buffer, or a hybridization buffer, compounds for preparing the reagents, and components for isolating the reagents.

VII. Definitions

Unless otherwise defined, all scientific and technical terms are used herein according to conventional usage, and have the same meaning as commonly understood by one of ordinary skill in the art to which the invention belongs. However, as used herein, the following definitions may be useful in aiding the skilled practitioner in understanding the invention:

"Modular molecular affinity clamp," "molecular affinity clamp" and "affinity clamp" (used interchangeably) are meant to refer to an affinity complex embodying the principles of the invention that has a bimodular architecture of two modules or domains which are linked together and bind the same target motif of interest. See PCT application PCT/US2008/083021 for a more detailed description of an affinity clamp.

The terms "target" and "target molecule," as used herein, refer to any biomolecule, substance or entity of interest for which an affinity ligand or clamp can be directly or indirectly coupled. Exemplary targets include, but are not limited to, peptide growth factors, pharmaceutical agents, cell signaling molecules, blood proteins, portions of cell surface receptor molecules, portions of nuclear receptors, steroid molecules, viral proteins, carbohydrates, enzymes, active sites of enzymes, binding sites of enzymes, portions of enzymes, small molecule drugs, cells, bacterial cells, proteins, epitopes of proteins, surfaces of proteins involved in protein-protein interactions, cell surface epitopes, diagnostic proteins, diagnostic markers, plant proteins, peptides involved in protein-protein interactions, and foods.

A "target motif", as used herein, refers to any portion or sequence of a biomolecule of interest for which a molecular affinity clamp is sought, e.g., refers to a pattern of amino acid residues which is recognized by particular recognition domains. In accordance with the invention, the target motif binds more than one recognition domain. In other words, a target motif is one to which an affinity clamp embodying the principles of the invention can bind with high affinity and specificity. Of particular importance are target motifs that are short peptides of about 2-100 amino acid residues, especially those of 3-10 amino acid residues.

As used herein, the term "binds" as used herein, refers to the interaction between a target motif and a recognition domain and indicates that the recognition domain associates with (e.g., interacts with or complexes with) the ligand or target motif to a statistically significant degree as compared to non-specific association.

In the context of an affinity clamp binding to a target motif, the term "greater affinity" indicates that an affinity clamp binds more tightly than a reference, or than the same domain in a reference condition, i.e., with a lower dissociation constant. In particular embodiments, the greater affinity is at least 2, 3, 4, 5, 6, 7, 8, 9, 10, 20-fold or more.

The term "linked" refers to any method of functionally connecting peptides, particularly affinity clamp domains. "Linked" may also refer to non-covalent physical association. The domains forming the affinity clamps may be linked covalently, e.g., via a peptide linkage, or non-covalently via a linker.

A "linker" or "linker moiety," (used interchangeably) may refer to a peptide sequence of about 30 or more amino acid residues that is configured to associate two affinity clamp domains in an orientation that facilitates binding the target motif or affinity ligand. The linker, generally, is bifunctional in that it includes a functionality for linking a first affinity domain (or other moiety) and a separate or similar functionality for linking a second affinity clamp domain (or other moiety).

As used herein, the terms "peptide," "polypeptide," and "protein" are used interchangeably and mean polymers of amino acid monomers linked by peptide linkages between carboxyl (COOH) groups and amine ($NH_2$) groups. A peptide may consist entirely of naturally occurring amino acid monomers, non-naturally occurring amino acids, or mixtures thereof. Unless denoted otherwise, whenever an amino acid sequence is represented, it will be understood that the amino acids are in N-terminal to C-terminal order from left to right. The term "polypeptide" may refer to small peptides, larger polypeptides, proteins containing single polypeptide chains, proteins containing multiple polypeptide chains, and multi-subunit proteins.

The term "amino acid", as used herein, refers to any amino acid, natural or non-natural, that may be incorporated, either enzymatically or synthetically, into a polypeptide or protein. Amino acids may also be altered. The term thus encompasses amino acids that have been modified naturally or by interaction. Examples may include, but are not limited to, phosphorylation, glycosylation, methylation, biotinylation, and any covalent and non-covalent additions to a protein that do not result in a change in amino acid sequence.

The term "label" as used herein refers to any tag, marker, or identifiable moiety. The skilled artisan will appreciate that many labels may be used in the methods of the invention. For example, labels include, but are not limited to, affinity ligands, fluorophores, radioisotopes, chromogens, dyes, magnetic probes, magnetic particles, paramagnetic particles, electrophoretic molecules and particles, dielectrophoretic particles, phosphorescence groups, chemiluminescent, mobility modifiers, and particles that confer a dielectrophoretic change.

As used herein in connection with numerical values, the terms "approximately" and "about" are meant to encompass variations of ±20% to ±10% or less of the indicated value.

VIII. Examples

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

A. Results

Binding Specificity of Affinity Clamps. Measurement of binding of affinity clamps to the homologous δ-catenin and ARVCF peptides suggested that, while ePDZ-a retained essentially the same binding specificity as the parent PDZ, the ePDZ-b family exhibited much higher specificity (Table 1). Because the C-terminal four residues are identical between these two peptides, these results indicate that ePDZ-b family clamps recognize one or more residues upstream of the core DSWV-COOH segment (Huang et al., 2008). To characterize the binding specificity of the ePDZ-b family clamps more comprehensively, selection of C-terminal peptide libraries in the phage-display format was performed. In this approach, multiple peptide sequences that bound to the ePDZ-b family clamps are identified from highly diverse libraries (Laura et al., 2002). The level of tolerance to mutations at particular positions in these peptides is used to deduce the binding specificity of the clamp.

Selection was performed using a library containing randomized amino acids at the seven C-terminal positions of the peptide. The inventors refer to the PDZ peptides using conventional numbering, i.e., the very C-terminal residue is designated as position 0 and the remaining positions are denoted with increasingly negative numbers toward the N-terminus as −1, −2 and so on. According to this numbering, the first library contains amino acids diversified from the −6 to 0 positions. The ePDZ-b family clamps preserved the underlying specificity of the parent PDZ domain with a motif (D(S/T)WV-COOH) as previously defined (Laura et al., 2002; Skelton et al., 2003; Zhang et al. 2006) and the amino acid compositions at −2 and 0 of this library was biased toward this motif, thereby reducing the sequence space that needed to be sampled. Namely, all the 20 amino acid types were introduced to position −1 and −3 to −6, a combination of S, T, A, V, I and F to position −2, and I, L, V, A, T and P to position 0. After three rounds of library sorting, binding clones for each ePDZ-b family member were obtained (FIG. 2 and FIG. 5). The C-terminal four positions (−3 to 0) converged completely to an Erbin PDZ motif, DTWV-COOH (SEQ ID NO:11), and positions −6 to −4 also showed appreciable levels of convergence. Ile, Leu and Met were found at the −4 position (Val in the original ARVCF target), Asn and Pro were common at the −5 position (originally Pro) and Gly and Ser were common at the −6 position (originally Gln). These results suggest that the ePDZ-b family clamps indeed specifically recognize a larger peptide segment than the recognition motif of the underlying PDZ domain, which predominantly recognizes the C-terminal four residues of the peptide.

To further characterize the sequence specificity of ePDZ-b family at the positions beyond the C-terminal D(S/T)WV segment, a second library was constructed in which the C-terminal four residues were fixed as DSWV and the five preceding positions were diversified with all 20 amino acids. Specificity profiles produced with this library were similar for ePDZ-b family members (FIG. 2). The motif for ePDZ-b was X-8(R)-7(G/M)-6X-5(I/L/M)-4, that for ePDZ-b1 was X-8(R)-7(G/S/neutral)-6X-5(I/L/M)-4, and ePDZ-b2 showed further convergence at the −5 position to N and S. The patterns of the N-terminal three residues did not resemble the ARVCF sequence (PQPVDSWV-COOH (SEQ ID NO:4S)) to which these affinity clamps were targeted, indicating that the affinity clamps could be further optimized to achieve higher binding affinity and possibly specificity. Indeed, a peptide designed to encode the most frequently observed amino acid at each position (RGSIDTWV-COOH (SEQ ID NO:1)) bound to ePDZ-b1 and ePDZ-b2 with eight-fold higher affinity relative to the ARVCF peptide. The dissociation half-life of the new peptide from ePDZ-b1 and ePDZ-b2 was about four hours. Compared with the binding motif of Erbin PDZ (ΦΦ(DE)(T/S)WV-COOH; Φ refers to a hydrophobic amino acid), the specificity profiles of ePDZ-b family were clearly more stringent and distinct at positions −4, −6 and −7, indicating that the domain interface evolution strategy can significantly expand the size of the recognition site beyond that of the capture domain.

TABLE 1

Sequences and binding parameters of affinity clamps.

| | BC loop | DE loop | FG loop | $K_{on}$ (M$^{-1}$S$^{-1}$) ARVCF | $K_{off}$ (S$^{-1}$) ARVCF | $K_d$ (nM) ARVCF | $K_d$ (nM) δ-catenin | Specificity Index[a] |
|---|---|---|---|---|---|---|---|---|
| Erbin PDZ | — | — | — | ND | ND | 2,200 | 6,300 | 3 |
| ePDZ-a | SYYGVS (SEQ NO: 23) | YSSS (SEQ NO: 13) | YSDYYGSHHY (SEQ NO: 14) | 2.9 × 10$^5$ | 1.5 × 10$^{-2}$ | 56 ± 5 | 429 | 8 |
| ePDZ-b | YYDSHVS (SEQ NO: 15) | GSKS (SEQ NO: 21) | HYNYHYYS (SEQ NO: 22) | 1.9 × 10$^5$ | 1.1 × 10$^{-2}$ | 56 ± 6 | >25,000 | >446 |
| ePDZ-b1 | YRELPVS SEQ NO: 20 | GSKS (SEQ NO: 21) | HYNYHYYS (SEQ NO: 22) | 7.3 × 10$^4$ | <3.7 × 10$^{-4}$ | <5 | >25,000 | >5,000 |
| ePDZ-b2 | FTDLPVS (SEQ NO: 16) | GSKS (SEQ NO: 21) | HYNYHYYS (SEQ NO: 22) | 7.0 × 10$^4$ | <2.9 × 10$^{-4}$ | <4 | >25,000 | >6,250 |

[a]The specificity index is defined as the ratio of the $K_d$ for δ-catenin to the $K_d$ for ARVCF.
ND, not detectable

TABLE 2

Data collection and refinement statistics for ePDZ-b1 (PDBID: 3CH8)

| Data collection statistic | |
|---|---|
| Space group | P3$_2$ |
| Cell parameters | a = b = 69.01 |
| | c = 46.71 |
| | α = β = 90 |
| | β = 120 |
| Beamline | APS-24ID-C |
| Wavelength | 1.0000 Å |
| Resolution (Å) (highest resolution shell)[a] | 20-1.8 (1.86-1.80) |
| Completeness(%) | 99.1 (97.0) |
| I/σ(I) | 23.74 (2.712) |
| $R_{merge}$[b] | 0.060 (0.512) |
| Average redundancy | 5.1 (3.9) |
| Refinement statistics | |
| Resolution range (Å) | 20.0-1.9 |
| Reflections used (free) | 18126 (973) |
| R factor[c] | 0.201 |
| $R_{free}$[d] | 0.260 |
| RMS deviations | |
| Bonds (Å) | 0.015 |
| Angles (°) | 1.620 |
| No. protein residues | 195 |
| No. waters | 89 |
| Average B factor (Å$^2$) | 58.92 |
| Ramachandran plot statistics | |
| Most favored (%) | 86.6 |
| Additionally allowed (%) | 12.1 |
| Generously allowed (%) | 1.3 |

[a] Highest resolution shell is shown in parenthesis.
[b] R-merge = $\Sigma_{hkl}\Sigma_i |I(hkl)_i - <I(hkl)>| / \Sigma_{hkl}\Sigma_i <I(hkl)_i>$ over i observations of a reflection hkl.
[c] R-factor = $\Sigma ||F(obs)| - |F(calc)|| / \Sigma |F(obs)|$.
[d] Rfree is R with 5% of reflections sequestered before refinement.

Alanine-scanning mutagenesis analysis. Although the phage-display library approach is powerful in determining general trends in sequence specificity, large-scale sequencing is necessary for quantitatively characterizing protein-interaction energetics (Skelton et al., 2003; Sidhu and Koide, 2007). This requirement is acute particularly when there is a strong amino acid preference and thus recovered clones are dominated by a particular pattern, as in our case above. Accordingly, to complement the library sorting experiments described above, the inventors performed Ala-scanning experiments of the ARVCF peptide coupled with affinity measurements using SPR. Because the goal was to understand the differences in target recognition of the affinity clamps, and because the sequence specificity of the C-terminal four residues is predominantly defined by the specificity of the parent PDZ domain, the inventors analyzed only those positions that differed between the ARVCF and δ-catenin peptides.

The effects of alanine substitution of the ARFCF peptide on its binding to ePDZ-a and the ePDZ-b family varied greatly. Significant decreases in binding (ΔΔG>1.0 kcal/mol; corresponding to >5-fold decrease in binding affinity) were observed for substitution at each of the four positions (positions −7 to −4) for ePDZ-b family members, whereas only small effects were seen for all four positions for ePDZ-a and Erbin PDZ (FIG. 2). The largest reduction (ΔΔG>3 kcal/mol) was observed at position −4 for all of the ePDZ-b family members. Also, alanine substitution primarily affected the dissociation rate of binding, and had only marginal effects on association rate, as often observed for this type of mutation (Zahnd et al., 2007). Taken together, both the Ala substitution results and the peptide library sorting results indicate that the significantly enhanced binding specificity of the ePDZ-b family is a result of their ability to recognize a larger segment of the target peptide than the PDZ domain.

The X-ray crystal structure of ePDZ-b1. To investigate the structural basis for the dramatically enhanced affinity and specificity of the ePDZ-b family affinity clamps, the inventors determined the X-ray crystal structure of ePDZ-b1 in complex with the ARVCF peptide at a 1.9 Å resolution. The statistics for data collection and refinement are shown in Table 2. Although we have been unable to determine the crystal structures of the other ePDZ-b family members, the inventors contemplate that other family members adopt similar overall structures and peptide-binding interfaces, given the few sequence differences and similar binding specificity profiles (Table 1).

The ePDZ-b1 structure has a clamp-like architecture as designed (FIG. 3). The rootmean-square deviations of the Cα atoms for the PDZ and FN3 domains (excluding the three mutated loops of the FN3 domain) are 0.973 Å and 0.752 Å relative to those of the ePDZ-a structure, respectively, indicating that the combination of the two domains and the mutations in the binding loops have not perturbed the fold of each domain. The electron density for the linker region (GGSGG (SEQ ID NO:17)) between the two domains was clearly observed, indicating that it is well ordered (FIG. 3).

The architecture can be described as a semi-open clamshell, with the peptide positioned along a long narrow cleft created at the domain junction. The FN3 domain is slanted to one side of the peptide-binding groove of the Erbin PDZ domain. Of the three diversified loops of FN3, the FG loop contacts both the PDZ domain and the peptide, the BC loop contacts only the PDZ domain and the DE loop does not contact either the PDZ domain or the peptide (FIG. 3). The affinity clamp buried 78% (966 Å2) of the solvent-accessible surface area of the peptide. The shape complementarity between FN3 and the PDZ/peptide complex as measured by the shape correlation value (Sc, 0.77) is quite high in comparison with other natural and engineered binding proteins (Lawrence and Coleman, 1993; Gilbreath et al., 2008). Together, these data indicate that the complex possesses a large and tightly packed interface.

TABLE 3

The dissociation constants (in nM) of clamp linker mutants to ARVCF peptide.

| Linker sequence | Affinity Clamp Used | | |
|---|---|---|---|
| | ePDZ-a | ePDZ-b | |
| GGSGG (wild type) | 56 | 56 | (SEQ ID NO: 17) |
| GGSG | 117 | 412 | (SEQ ID NO: 18) |
| GGS | 134 | >5,000 | |
| GG | 311 | >10,000 | |
| GGSGGGSGGS | 245 | 247 | (SEQ ID NO: 19) |

Peptide/ePDZ-b1 Interactions. In the ePDZ-b 1 structure, the C-terminal four residues of the ARVCF peptide are inserted into the Erbin PDZ ligand-binding groove in a manner similar to the previously reported structure of a homologous peptide bound to Erbin-PDZ (Skelton et al., 2003). This explains the observation that ePDZ-b1 preserved the underlying binding specificity of Erbin-PDZ. Unlike the C-terminal residues that are sandwiched between the two domains, the N-terminal four residues (positions −7 to −4) of the peptide extend onto the FN3 domain, participating in an extended hydrogen bond network and making extensive hydrophobic contacts primarily with the FG loop of FN3 domain (FIG. 4). Nearly 50% of the total surface areas of the N-terminal four residues were buried in the complex (FIG. 4). Therefore, the recognition of a larger portion of the peptide by ePDZ-b1 is corroborated by these results, and provides a structural basis for the specificity enhancement exhibited by the ePDZ-b family.

The ePDZ-b1 structure explains the role of V-4 in ligand recognition, as shown in phage-display and alanine-scanning experiments, and rationalizes the puzzling observation of the reduced affinity of ePDZ-b family members to the δ-catenin peptide relative to the starting PDZ domain (Table 1). V-4 is nearly completely buried in ePDZ-b1 (FIG. 4) with two side-chain methyl groups forming hydrophobic contacts with residues H182, Y183, Y184 in the FG loop of FN3. The substitution of Val with Pro would introduce steric clashes with the nearby Y181 on the FG loop of the FN3 domain, which should result in reduced affinity. The peptide library results suggest a preference for I/L/M at this position over Val (FIGS. 2 and 5). There is a small cavity around V-4 that could accommodate a larger aliphatic side chain. Consequently, substitution of I/L/M side chains at this position may supply additional van der Waals contacts that contribute to enhanced affinity.

The peptide library experiments revealed a strong preference for Arg at position −7 even though the original target had Pro at this position. In the structure, Pro-7 is sandwiched by the side chains of Y183 and R136 of FN3 but the packing of these residues does not appear optimal (FIG. 4), suggesting the flexible Arg side chain at the −7 position may fit better in this cavity. The Arg side chain could also form a salt bridge with E150 on FN3 and stabilize the peptide clamp interaction.

The ePDZ-b family members differ only in the BC loop sequence (Table 1), and thus a >10 fold affinity enhancement for ePDZ-b1 and ePDZ-b2 over ePDZ-b can be attributed to the BC loop alterations. The BC loop sequence, YYDSHVS, of ePDZ-b was replaced with YRELPVS in ePDZ-b1 and FTDLPVS in ePDZ-b2 (Table 1). Together these mutants differ at only five residues in the BC loop, two of which may be considered conservative substitutions (Y to F at position 127 and D to E at position 129). R128 in ePDZ-b1 (Y in ePDZ-b and T in ePDZ-b2) is located away from the domain interface. However, ePDZ-b1 and -b2 both have L130 and P131, and they are likely to be involved in affinity enhancement (Table 1). In the ePDZ-b1 structure, P131 is part of a turn that places the side chain of L130 into the PDZ/FN3 interface. These two residues form extensive hydrophobic contacts with residues P18, F19, T29, R30 and P43 of the PDZ domain. L130 and P131 also form hydrophobic contacts with residues H178, Y179 and Y184 on the FG loop of FN3 domain. Therefore, L130 and P131 are likely to play an important role in reducing the inter-domain movement, which should entropically favor target binding, and/or stabilize a favorable FG loop conformation for peptide binding. These results further demonstrate that the FN3 loops can affect affinity and specificity by a mechanism that indirectly alters the binding interface and/or dynamic properties.

Comparison of Affinity Clamp Structures. The ePDZ-b1 structure and the previously reported ePDZ-a structure (Huang et al., 2008) offer an opportunity to understand how the combination of the same two protein domains (except for the FN3 loops) can generate a dramatic difference in the levels of binding specificity. In ePDZ-a, the FN3 loops nearly completely cover the C-terminal four residues of the peptide, but the N-terminal two residues of the peptide are largely exposed (FIG. 4). The FN3 domain sits diagonally over the peptide bound to PDZ (FIG. 3). The BC and FG loops interact with the peptide from the V0 to P-5 positions and also with adjacent PDZ residues (FIG. 3). This mode of interaction is distinct from that found for ePDZ-b1 described above (FIG. 3). The N-terminal four residues account for nearly 50% of total peptide surface burial for ePDZ-b1, but less than 25% for ePDZ-a.

The superposition of the PDZ domain of the two structures revealed a drastic difference in the position of the FN3 domain. The FN3 portions of the two affinity clamps are related by a 14 Å parallel translation (FIG. 3), which is responsible for the recognition of different portions of the peptide by FN3 of the two affinity clamps. In contrast, the interaction of the peptide with the PDZ domain is conserved, as expected (FIG. 4). Because the two domains are loosely linked, the domain-interface is inherently plastic. This plasticity allows for the translational displacement of the FN3 domain to create a different peptide "read-out" mode and thus different levels of binding specificity.

Roles of the linker connecting the two domains. Another intriguing difference between the structures of these two affinity clamps is that the linker is well-ordered in ePDZ-b 1 but disordered in ePDZ-a. These observations suggest that the linker for ePDZ-b1 may play an active role in forming the clamp architecture, whereas the ePDZ-a linker may be highly flexible and simply connecting the two domains (FIG. 3). The distance between the C-terminus of PDZ (D97) and the N-terminus of FN3 (V103) in both structures is similar (~P12 Å). In ePDZ-a, the residues around the linker form a concave surface in which the linker may fluctuate (FIG. 5). In contrast, the residues around the linker of ePDZ-b 1 form a convex surface that interacts with the linker through extensive hydrogen bonds and hydrophobic contacts (FIG. 3).

To examine the role of the linker, affinity clamps were constructed with linkers of different lengths and measured their binding affinity to the target peptide. For both ePDZ-a and ePDZ-b, the original linker gave the highest affinity, indicating that the peptide-binding interface has been optimized in the context of a particular linker length. ePDZ-a and ePDZ-b showed significantly different levels of sensitivity to changes in linker length. ePDZ-a is not highly sensitive to either shortening or lengthening of the linker, while ePDZ-b is very sensitive to linker shortening. The removal of one Gly reduced the binding affinity by eight fold and the removal of two Gly eliminated detectable binding to the target peptide. ePDZ-b was not as sensitive to linker extension. In the crystal structure, the linker in ePDZ-b1 appears already stretched, but the residues adjacent to the linker, i.e., the C-terminal part of PDZ domain and the N-terminal part of the FN3 domain, appear relatively flexible as judged by the crystallographic B-factor. Although the structural data suggest that these residues may be able to provide "play" that compensates for linker shortening, the results of linker mutation indicate that such adjustment was not sufficient to counteract for the two-residue deletion. Together, these results indicate that the linker between the two domains of affinity clamps clearly impacts the range of accessible inter-domain geometry and thus it is an important parameter to consider in designing affinity clamps.

Comparison of affinity clamp and epitope tag to anti-GFP antibody and GFP tag. FIG. 6. shows filament gliding velocity histograms. The affinity clamp protein or anti-GFP antibody was immobilized on the coverslip surface then the tagged motor protein was allowed to bind. Filaments were introduced and bound to the motor protein without ATP. After motility solution with ATP was added the filaments moved along the surface. 45 filaments were analyzed for each regime by tracking filament ends as they moved. Data was plotted as a histogram and fit to a Gaussian distribution. Note that the data with the affinity clamp has a narrower distribution. This may be because the anti-GFP binds more weakly to the tagged protein bound to actin or the linkage and the presentation of the motor off the surface is more robust with the clamp. The difference in the absolute velocity may be due to different sample preparations and thus its significance needs to be confirmed.

Labeling with epitope tag and holding force of the affinity clamp to the epitope. Single Myosin X motors with the affinity clamp recognition sequence were surface immobilized using the affinity clamp. An optically trapped actin dumb-bell was brought into proximity. As the motor interacted with the actin filament, the stage was jumped by approximately 300 nm displacing the dumb-bell out of the traps. This imposes a high force (~30 pN) on the actin-motor-affinity clamp complex. The motor then unbinds actin and the dumb-bell relaxes to the original position. Five such events are shown in the figure. The fact that the repetitive responses can be observed indicates that the affinity clamp-motor linkage remains intact after repeated applications of the high force.

FIG. 8 illustrates TIRF sequence. The single cysteine of the clamp protein was conjugated to a Cy-5 dye via a maleimide linkage. Labeled clamp was mixed with a low dilution of motor and introduced to the experimental flow cell with fascin-actin bundled adhered to the surface via biotin/neutravidin. Single processive motor events were imaged by TIRF microscopy. One such event is represented here with a series of frames separated by 2 seconds. These results demonstrate the utility of the clamp-tag system for specific labeling.

FIG. 9 shows the surface plasmon resonance analyses of the interactions between affinity clamps and peptide tags. The affinity clamps were immobilized and the target peptides in the form of yeast SUMO fusion protein were used as the analytes. (a) Sensorgrams for the interaction of the wild-type ARVCF peptide and ePDZ-b2. Data with 0, 10, 20, 40, 80 and 160 nM peptide are shown in black, and calculated curves from the global fittings of the 1:1 Langmuir binding model are in orange. The estimated dissociation constant is indicated. The peptide sequence is also shown. (b) Sensorgrams for the interaction of the new tag peptide to ePDZ-b2. Data with 0, 10, 20, 40 and 80 nM target are shown. Note that the new tag peptide has higher affinity and that its dissociation rate is much slower than the original peptide.

B. Methods

C-terminal peptide library construction and sorting. The peptide libraries were constructed as a fusion to the C-terminus of a M13 P8 protein mutant following the method of Laura et al. (2002). A gene for mutant p8 was constructed from synthesized oligonucleotides and cloned between the BamHI and HindIII site of a vector containing OmpT signal sequence originally used for phage display of a single-domain antibody (Koide and Koide, 2007). Peptide libraries were made using the Kunkel mutagenesis method as described (Koide et al., 1998; Koide and Koide, 2007). The hexta-peptide library contained $1 \times 10^9$ independent clones and the penta-peptide library contained $3 \times 10^8$ independent clones. The phage particles were propagated in E. coli XL1-blue with M13-KO7 helper phage and 10 μM IPTG following procedures described previously (Huang et al., 2008).

To facilitate immobilization of affinity clamps in library sorting, a Cys residue was added to the C-terminus to which biotin was chemically conjugated using EZ-Link Biotin-HPDP ((N-(6-(Biotinamido)hexyl)-3'-(2'-pyridyldithio)-propionamide; Thermo Scientific). The C17 terminus of the affinity clamp is located away from the binding site and thus the addition of the Cys residue and subsequent biotinylation did not affect their binding function.

Phage-display library sorting was performed using biotinylated affinity clamps and streptavidin-coated magnetic beads (Streptavidin MagneSphere Paramagnetic Particles; Promega). A library solution was incubated with 1 μM of biotinylated affinity clamp for 30 min at room temperature, and then the mixture was captured by streptavidin-coated magnetic beads. After washing the beads three times with TBST (150 mM NaCl, 50 mM Tris-HCl, pH7.5, and 0.5% Tween 20), the phage-streptavidin beads mixture was used to infect E. coli XL1-blue and the phage particles were prepared as described above. The subsequent three rounds of sorting were performed using a Kingfisher instrument (Thermo Scientific) as previously described (Huang et al., 2008) with 400, 200 and 200 nM of ePDZ-b and 200, 100 and 100 nM of ePDZ-b1 and ePDZ-b2, respectively. Positive clones were identified using phage ELISA and their sequences were deduced using DNA sequencing (Koide and Koide, 2007).

Protein Expression and Purification. All proteins used in this study were expressed using derivatives of the pHFT2 expression vector in E. coli BL21(DE3) cells. Protein expression was induced with 500 μM IPTG for three to five hours at 25° C. Proteins were purified with Ni affinity chromatography following standard protocols. When necessary, a second step of purification with Sephacryl S-100 column in PBS (50 mM sodium phosphate containing 150 mM NaCl, pH 7.4) was performed to ensure that proteins were monomeric. For protein crystallization and SPR experiments, the N-terminal His tag was cleaved with TEV protease and the cleaved protein was purified using Ni affinity chromatography.

Site-directed mutagenesis. Mutant forms of the SUMO-ARVCF peptide fusion protein and linker mutants of affinity clamps were constructed using Kunkel mutagenesis.

Affinity Measurements. SPR measurements were performed in 20 mM HEPES/NaOH buffer (pH 7.4), 150 mM NaCl, and 0.005% Tween 20 at 25° C. on a BIAcore 2000 instrument. The affinity clamp or the linker mutant was immobilized on a Ni-NTA chip to the level of approximate 300 RU, and different concentrations of SUMO-peptide fusion protein were injected. The kinetic data were analyzed using the one-to-one binding model in BIAEvaluation (BIAcore). For weak interactions (Kd>5 μM), Kd values were determined from the saturation curve of the maximum RU values.

X-ray Crystallography. The ePDZ-b1 protein was dialyzed in 20 mM Tris-HCl buffer pH 7.4 containing 100 mM NaCl, concentrated to ~15 mg/ml and mixed with the ARVCF peptide at a 1:1.2 ratio. The ePDZ-b1/ARVCF peptide complex was crystallized in 31% isopropanol, 0.1M HEPES pH 7.5, 0.2 M MgCl$_2$ by using the hanging drop vapor diffusion method at 20° C. Crystals were cryoprotected in the mother solution containing 20% glycerol and flash-frozen in liquid nitrogen. The X-ray data were collected at the Advanced Photon Source (Argonne National Laboratory) beamline 24-ID-C by oscillation method. X-ray diffraction data were processed with HKL2000 (Otwinowski and Minor, 1997). The structure was determined by molecular replacement with the program MOLREP in CCP4. The structures of an FN3 mutant (PDB ID code 2OBG) and Erbin PDZ domain (PDB ID code 1 MFG) were used as the search models. Refmac528 was used for the structural refinement. Model building was carried out by using the program Coot (Emsley and Cowtan, 2004). The structure of the engineered loops, linker, and ARVCF peptide were built at this stage. Molecular graphics were generated using Pymol (on the world wide web at pymol.org). Solvent accessible surface areas were calculated using Areaimol in CCP4. For the analysis of MHC-peptide interfaces, the following coordinates were used: 1G6R, 1BD2, 1KJ2, 1LP9, 1MI5, 2GJ6, and 1FO0.

Accession Number. Coordinates and structure factors have been deposited in the Protein Data Bank with accession number 3CH8.

REFERENCES

The following references, to the extent that they provide exemplary procedural or other details supplementary to those set forth herein, are specifically incorporated herein by reference.

U.S. Pat. No. 4,879,236
U.S. Pat. No. 5,871,986
U.S. Patent Publn. 20030143598
U.S. Patent Publn. 20030175702
U.S. Patent Publn. 20080050731
U.S. Patent Publn. 20090023157
U.S. Patent Publn. PCT/US2008/083021
Angel et al., Cell, 49:729, 1987a.
Angel et al., Cell, 49:729, 1987b.
Atchison and Perry, Cell, 46:253, 1986.
Atchison and Perry, Cell, 48:121, 1987.
Ausubel et al., In: Current Protocols in Molecular Biology, John, Wiley & Sons, Inc, NY, 1994; 1996.
Banerji et al., Cell, 27:299, 1981.
Banerji et al., Cell, 33(3):729-740, 1983.
Barany and Merrifield, In: The Peptides, Gross and Meienhofer (Eds.), Academic Press, NY, 1-284, 1979.
Berkhout et al., Cell, 59:273-282, 1989.

Blagoev et al., *Nat. Biotechnol.*, 21:315-8, 2003.
Blanar et al., *EMBO J.*, 8:1139, 1989.
Bodine and Ley, *EMBO J.*, 6:2997, 1987.
Boshart et al., *Cell*, 41:521, 1985.
Bosze et al., *EMBO J.*, 5(7):1615-1623, 1986.
Braddock et al., *Cell*, 58:269, 1989.
Bruchez et al., *Science*, 281:2013-2016, 1998.
Bulla and Siddiqui, *J. Virol.*, 62:1437, 1986.
Campbell and Villarreal, *Mol. Cell. Biol.*, 8:1993, 1988.
Campere and Tilghman, *Genes and Dev.*, 3:537, 1989.
Campo et al., *Nature*, 303:77, 1983.
Celander and Haseltine, *J. Virology*, 61:269, 1987.
Celander et al., *J. Virology*, 62:1314, 1988.
Chang et al., *Mol. Cell. Biol.*, 9:2153, 1989.
Chatterjee et al., *Proc. Natl. Acad. Sci. USA*, 86:9114, 1989.
Choi et al., *J. Mol. Biol.*, 262(2):151-167, 1996.
Cohen et al., *J. Cell. Physiol.*, 5:75, 1987.
Costa et al., *Mol. Cell. Biol.*, 8:81-90, 1988.
Cripe et al., *EMBO J.*, 6:3745, 1987.
Crowther, In: *Theory and Practice*, Methods in Molecular Biol., 42-ELISA, Humana Press, NJ, 1995.
Culotta and Hamer, *Mol. Cell. Biol.*, 9:1376-1380, 1989.
Dandolo et al., *J. Virology*, 47:55-64, 1983.
Deschamps et al., *Science*, 230:1174-1177, 1985.
Edbrooke et al., *Mol. Cell. Biol.*, 9:1908-1916, 1989.
Edlund et al., *Science*, 230:912-916, 1985.
Emsley and Cowtan, *Acta Crystallogr. D. Biol. Crystallogr.*, 60:2126-32, 2004.
Feng and Holland, *Nature*, 334:6178, 1988.
Firak and Subramanian, *Mol. Cell. Biol.*, 6:3667, 1986.
Foecking and Hofstetter, *Gene*, 45(1):101-105, 1986.
Fujita et al., *Cell*, 49:357, 1987.
Gilbreath et al., *J. Mol. Biol.*, 381:407-418, 2008.
Gillies et al., *Cell*, 33:717, 1983.
Gloss et al., *EMBO J.*, 6:3735, 1987.
Godbout et al., *Mol. Cell. Biol.*, 8:1169, 1988.
Goodbourn and Maniatis, *Cell*, 41(2):509-520, 1985.
Goodbourn et al., *Cell*, 45:601, 1986.
Greene et al., *Immunology Today*, 10:272, 1989.
Grosschedl and Baltimore, *Cell*, 41:885, 1985.
Hampl et al., *Anal. Biochem.*, 288:176-187, 2001.
Harlow and Lane, In: *Antibodies: A Laboratory Manual*, Cold Spring Harbor Laboratory, Cold Spring Harbor, N.Y., 553-612, 1988.
Harma et al., *Clin. Chem.*, 47:561-568, 2001.
Haslinger and Karin, *Proc. Natl. Acad. Sci. USA*, 82:8572, 1985.
Hauber and Cullen, *J. Virology*, 62:673, 1988.
Hen et al., *Nature*, 321:249, 1986.
Hensel et al., *Lymphokine Res.*, 8:347, 1989.
Herr and Clarke, *Cell*, 45:461, 1986.
Hirochika et al., *J. Virol.*, 61:2599, 1987.
Hirsch et al., *Mol. Cell. Biol.*, 10:1959, 1990.
Holbrook et al., *Virology*, 157:211, 1987.
Horlick and Benfield, *Mol. Cell. Biol.*, 9:2396, 1989.
Huang et al., *Cell*, 27:245, 1981.
Huang et al., *Proc. Natl. Acad. Sci. USA*, 105:6578-83, 2008.
Hug et al., *Mol. Cell. Biol.*, 8:3065-3079, 1988.
Hwang et al., *Mol. Cell. Biol.*, 10:585, 1990.
Imagawa et al., *Cell*, 51:251, 1987.
Imbra and Karin, *Nature*, 323:555, 1986.
Imler et al., *Mol. Cell. Biol.*, 7:2558, 1987.
Imperiale and Nevins, *Mol. Cell. Biol.*, 4:875, 1984.
Jakobovits et al., *Mol. Cell. Biol.*, 8:2555, 1988.
Jameel and Siddiqui, *Mol. Cell. Biol.*, 6:710, 1986.
Jaynes et al., *Mol. Cell. Biol.*, 8:62, 1988.
Johnson et al., *Mol. Cell. Biol.*, 9(8):3393-3399, 1989.
Kadesch and Berg, *Mol. Cell. Biol.*, 6:2593, 1986.
Karin et al., *Mol. Cell. Biol.*, 7:606, 1987.
Karin et al., *Mol. Cell. Biol.*, 7:606, 1987.
Katinka et al., *Cell*, 20:393, 1980.
Katinka et al., *Nature*, 290:720, 1981.
Kawamoto et al., *Mol. Cell. Biol.*, 8:267, 1988.
Kiledjian et al., *Mol. Cell. Biol.*, 8:145, 1988.
Klamut et al., *Mol. Cell. Biol.*, 10:193, 1990.
Koch et al., *Mol. Cell. Biol.*, 9:303, 1989.
Koide and Koide, *Methods Mol. Biol.*, 352:95-109, 2007.
Koide et al., *J. Mol. Biol.*, 284:1141-1151, 1998.
Kriegler and Botchan, *Mol. Cell. Biol.*, 3:325, 1983.
Kriegler et al., *Cell*, 38:483, 1984a.
Kriegler et al., In: *Cancer Cells 2/Oncogenes and Viral Genes*, Van de Woude et al. eds, Cold Spring Harbor, Cold Spring Harbor Laboratory, 1984b.
Kuhl et al., *Cell*, 50:1057, 1987.
Kunz et al., *Nucl. Acids Res.*, 17:1121, 1989.
Larsen et al., *Proc. Natl. Acad. Sci. USA*, 83:8283, 1986.
Laspia et al., *Cell*, 59:283, 1989.
Latimer et al., *Mol. Cell. Biol.*, 10:760, 1990.
Laura et al., *J. Biol. Chem.*, 277:12906-14, 2002.
Lawrence and Coleman, *J. Mol. Biol.*, 234:946-50, 1993.
Lee et al., *Nature*, 294:228, 1981.
Lee et al., *Nucleic Acids Res.*, 12:4191-206, 1984.
Lin et al., *Mol. Cell. Biol.*, 10:850, 1990.
Luria et al., *EMBO J.*, 6:3307, 1987.
Lusky and Botchan, *Proc. Natl. Acad. Sci. USA*, 83:3609, 1986.
Lusky et al., *Mol. Cell. Biol.*, 3:1108, 1983.
Majors and Varmus, *Proc. Natl. Acad. Sci. USA*, 80:5866, 1983.
McNeall et al., *Gene*, 76:81, 1989.
Merrifield, *Science*, 232(4748):341-347, 1986.
Miksicek et al., *Cell*, 46:203, 1986.
Mordacq and Linzer, *Genes and Dev.*, 3:760, 1989.
Moreau et al., *Nucl. Acids Res.*, 9:6047, 1981.
Mrksich, *ACS Nano*, 2(1):7-18, 2008.
Muesing et al., *Cell*, 48:691, 1987.
Neuberger et al., *Nucleic Acids Res.*, 16(14B):6713-6724, 1988.
Ng et al., *Nuc. Acids Res.*, 17:601, 1989.
Okana et al., *Anal. Biochem.*, 202:120-125, 1992.
Omitz et al., *Mol. Cell. Biol.*, 7:3466, 1987.
Ondek et al., *EMBO J.*, 6:1017, 1987.
Otwinowski and Minor, *Methods Enzymol.*, 276:307-26, 1997.
Palmiter et al., *Cell*, 29:701, 1982.
Pawson and Nash, *Science*, 300:445-52, 2003.
Pech et al., *Mol. Cell. Biol.*, 9:396, 1989.
Perez-Stable and Constantini, *Mol. Cell. Biol.*, 10:1116, 1990.
Perlmann and Perlmann, In: *Cell Biology: A Laboratory Handbook*. San Diego, Calif., Academic Press, Inc., 322-328, 1994.
Picard and Schaffner, *Nature*, 307:83, 1984.
Pinkert et al., *Genes and Dev.*, 1:268, 1987.
Ponta et al., *Proc. Natl. Acad. Sci. USA*, 82:1020, 1985.
Poon, *Expert Rev. Proteomics*, 4(1):51-65, 2007.
Queen and Baltimore, *Cell*, 35:741, 1983.
Quinn et al., *Mol. Cell. Biol.*, 9:4713, 1989.
Redondo et al., *Science*, 247:1225, 1990.
Reisman and Rotter, *Mol. Cell. Biol.*, 9:3571, 1989.
Resendez Jr. et al., *Mol. Cell. Biol.*, 8:4579, 1988.
Rimmele, *Chembiochem.*, 4:963-71, 2003.
Rippe et al., *Mol. Cell. Biol.*, 9(5):2224-22277, 1989.
Rittling et al., *Nucl. Acids Res.*, 17:1619, 1989.

Sambrook and Russell, Molecular Cloning: A Laboratory Manual 3rd Ed., Cold Spring Harbor Laboratory Press, 2001.
Schaffner et al., *J. Mol. Biol.,* 201:81, 1988.
Searle et al., *Mol. Cell. Biol.,* 5:1480, 1985.
Sharp and Marciniak, *Cell,* 59:229, 1989.
Shaul and Ben-Levy, *EMBO J.,* 6:1913, 1987.
Sherman et al., *Mol. Cell. Biol.,* 9:50, 1989.
Sidhu and Koide, *Curr. Opin. Struct. Biol.,* 17:481-7, 2007,
Sjolander and Urbaniczky, *Anal. Chem.,* 63:2338-2345, 1991.
Skelton et al., *J. Biol. Chem.,* 278:7645-54, 2003.
Sleigh and Lockett, *J. EMBO,* 4:3831, 1985.
Spalholz et al., *Cell,* 42:183, 1985.
Spandau and Lee, *J. Virology,* 62:427, 1988.
Spandidos and Wilkie, *EMBO J.,* 2:1193, 1983.
Stears et al., *Physiol. Genomics,* 3:93-99, 2000.
Stephens and Hentschel, *Biochem. J.,* 248:1, 1987.
Stewart and Young, In: *Solid Phase Peptide Synthesis,* 2d. ed., Pierce Chemical Co., 1984.
Stimpson et al., *Proc. Natl. Acad. Sci. USA,* 92:6379-6383, 1995.
Stuart et al., *Nature,* 317:828, 1985.
Sullivan and Peterlin, *Mol. Cell. Biol.,* 7:3315, 1987.
Swartzendruber and Lehman, *J. Cell. Physiology,* 85:179, 1975.
Szabo et al., *Curr. Opin. Struct. Biol.,* 5:699-705, 1995.
Takebe et al., *Mol. Cell. Biol.,* 8:466, 1988.
Tam et al., *J. Am. Chem. Soc.,* 105:6442, 1983.
Tavernier et al., *Nature,* 301:634, 1983.
Taylor and Kingston, *Mol. Cell. Biol.,* 10:165, 1990a.
Taylor and Kingston, *Mol. Cell. Biol.,* 10:176, 1990b.
Taylor et al., *J. Biol. Chem.,* 264:15160, 1989.
Thiesen et al., *J. Virology,* 62:614, 1988.
Treisman, *Cell,* 42:889, 1985.
Tronche et al., *Mol. Biol. Med.,* 7:173, 1990.
Tronche et al., *Mol. Cell. Biol.,* 9:4759, 1989.
Trudel and Constantini, *Genes and Dev.,* 6:954, 1987.
Tyndall et al., *Nuc. Acids. Res.,* 9:6231, 1981.
Vasseur et al., *Proc. Natl. Acad. Sci. USA,* 77:1068, 1980.
Wang and Calame, *Cell,* 47:241, 1986.
Wang et al., *Anal. Chem.,* 72:5907-5917, 2000.
Weber et al., *Cell,* 36:983, 1984.
Winoto and Baltimore, *Cell,* 59:649, 1989.
Yan et al., *Front. Biosci.,* 10:1802-27, 2005.
Yutzey et al. *Mol. Cell. Biol.,* 9:1397, 1989.
Zahnd et al., *J. Mol. Biol.,* 369:1015-28, 2007.
Zhang et al., *J. Biol. Chem.,* 281:22299-311, 2006.

The invention claimed is:

1. A method of detecting a target comprising an affinity ligand having a carboxy terminal amino acid sequence of RGSIDTWV (SEQ ID NO: 1) comprising contacting the target with a binding agent that specifically binds the affinity ligand having a carboxy terminal amino acid sequence of RGSIDTWV (SEQ ID NO: 1) and detecting the complex between the affinity ligand and the binding agent.

2. The method of claim 1, wherein the affinity ligand is coupled to a first label and the binding agent is coupled to a second label.

3. The method of claim 2, wherein the first and the second label are a donor/acceptor pair.

4. The method of claim 1, wherein the binding agent is a molecular affinity clamp that specifically binds the affinity ligand having a carboxy terminal amino acid sequence of RGSIDTWV (SEQ ID NO:1).

5. The method of claim 4, wherein the molecular affinity clamp is an ePDZ-b molecular affinity clamp.

6. The method of claim 1, wherein the target is a peptide, a polypeptide, a particle, a cell, a macromolecular complex, or a small molecule.

7. The method of claim 1, wherein the target is a fusion protein.

8. The method of claim 7, wherein the target comprises a second detectable amino acid sequence.

9. The method of claim 8, wherein the second detectable amino acid sequence is a myc tag, a poly-His tag, a GST tag, a Flag tag, a fluorescent tag or a luminescent tag.

10. The method of claim 9, wherein the fluorescent tag is GFP.

11. The method of 9, wherein the luminescent tag is luciferase.

12. The method of claim 9, wherein the poly-His tag is a hexa-histidine amino acid sequence.

13. The method of claim 7, wherein the target comprises a cleavage site terminal to the affinity ligand.

14. The method of claim 13, wherein the cleavage site is a protease cleavage site.

15. The method of claim 14, wherein the protease cleavage site is a trypsin, calpain, carboxypeptidase, chymotrypsin, V8 protease, pepsin, papain, subtilisin, thrombin, elastase, glue-C, endo lys-C, proteinase K, caspase-1, caspase-2, caspase-3, caspase-4, caspase-5, caspase-6, caspase-7, caspase-8, MetAP-2, adenovirus protease, or HIV protease cleavage site.

16. The method of claim 2, wherein the first label is a dye, a quencher, a reporter protein, radiolabel, or a quantum dot.

17. The method of claim 2, wherein the second label is a dye, a quencher, a reporter protein, radiolabel, or a quantum dot.

18. The method of claim 3, wherein the donor/acceptor pair is a fluorescent resonance energy transfer (FRET) donor/acceptor pair.

19. The method of claim 3, wherein the molecular affinity clamp has a dissociation constant for the affinity ligand equal or lower than 500 pM.

20. The method of claim 3, wherein the molecular affinity clamp has a dissociation constant for the affinity ligand equal or lower than 1 μM.

* * * * *

UNITED STATES PATENT AND TRADEMARK OFFICE
CERTIFICATE OF CORRECTION

| | | |
|---|---|---|
| PATENT NO. | : 8,263,350 B2 | Page 1 of 1 |
| APPLICATION NO. | : 12/826322 | |
| DATED | : September 11, 2012 | |
| INVENTOR(S) | : Shohei Koide et al. | |

It is certified that error appears in the above-identified patent and that said Letters Patent is hereby corrected as shown below:

In claim 15, column 45, line 20, delete "glue-" and insert --gluc- -- therefor.

Signed and Sealed this
Twenty-seventh Day of November, 2012

David J. Kappos
*Director of the United States Patent and Trademark Office*